United States Patent
Menon et al.

(10) Patent No.: US 9,933,343 B2
(45) Date of Patent: Apr. 3, 2018

(54) INTEGRATED MEMBRANE FOR PRESERVATION OF BIOMOLECULES

(71) Applicant: ChromoLogic LLC, Pasadena, CA (US)

(72) Inventors: Naresh Menon, Pasadena, CA (US); Peter Bui, Pasadena, CA (US); Cheryl Tan, Pasadena, CA (US)

(73) Assignee: CHROMOLOGIC LLC, Monrovia, CA (US)

(*) Notice: Subject to any disclaimer, the term of this patent is extended or adjusted under 35 U.S.C. 154(b) by 338 days.

(21) Appl. No.: 13/829,824

(22) Filed: Mar. 14, 2013

(65) Prior Publication Data

US 2014/0273058 A1 Sep. 18, 2014
US 2016/0349156 A9 Dec. 1, 2016

Related U.S. Application Data

(60) Provisional application No. 61/685,330, filed on Mar. 14, 2012.

(51) Int. Cl.
*G01N 1/40* (2006.01)
*G01N 1/31* (2006.01)

(52) U.S. Cl.
CPC .............. *G01N 1/31* (2013.01); *G01N 1/405* (2013.01)

(58) Field of Classification Search
CPC ........... G01N 15/0272; G01N 15/0618; G01N 2021/8571; G01N 2035/00475; G01N 2035/1053
USPC ........................................................ 422/69
See application file for complete search history.

(56) References Cited

U.S. PATENT DOCUMENTS

| | | | | |
|---|---|---|---|---|
| 4,362,618 A | * | 12/1982 | Cook et al. | 210/275 |
| 8,247,545 B1 | * | 8/2012 | Colpan | 536/25.4 |
| 2006/0147349 A1 | * | 7/2006 | Rhodes | 422/100 |
| 2006/0240409 A1 | * | 10/2006 | Prince et al. | 435/5 |
| 2007/0161030 A1 | * | 7/2007 | Patton | G01N 27/44747 435/6.12 |

(Continued)

OTHER PUBLICATIONS

Alvarez-Garcia, Ines et al.; "MicroRNA functions in animal development and human disease"; The Company of Biologists 2005; Development 132; pp. 4653-4662.

(Continued)

*Primary Examiner* — Paul S Hyun
(74) *Attorney, Agent, or Firm* — Lewis Roca Rothgerber Christie LLP

(57) ABSTRACT

The apparatus of the present invention comprises an integrated membrane for separation and preservation of biomolecules. Biomolecules, such as those in blood, can be separated and preserved. The apparatus includes a housing having a matrix portion, and a fluid collection portion disposed within an inner cavity. The housing further includes an aperture permitting access to the inner cavity. The apparatus also includes a matrix disposed within the matrix portion. The matrix includes a first layer for collecting cells from the fluid, a second layer for protein adsorption, and a third layer for nucleic acid adsorption. Fluid enters the housing through the aperture, passes through the matrix, and into the fluid collection portion. Cells from the fluid in a layer of the matrix are collected; adsorbing protein from the fluid in a layer of the matrix; and adsorbing nucleic acid from the fluid in a layer of the matrix.

21 Claims, 11 Drawing Sheets

(56) References Cited

U.S. PATENT DOCUMENTS

| | | | |
|---|---|---|---|
| 2008/0113357 A1* | 5/2008 | Baggio et al. | 435/6 |
| 2010/0059440 A1* | 3/2010 | Rudstedt et al. | 210/651 |
| 2011/0146418 A1* | 6/2011 | Brevnov | G01N 1/4005 |
| | | | 73/863.23 |

OTHER PUBLICATIONS

Bertheau, Y. et al.; "Persistence of Plant DNA Sequences in the Blood of Dairy Cows Fed with Genetically Modified (Bt176) and Conventional Corn Silage"; J. Agric. Food Chem.; 2009; 57; pp. 509-516.

Blondal, Thorarinn et al.; "Assessing sample and miRNA profile quality in serum and plasma or other biofluids"; Methods 59; 2013; pp. S1-S6.

Crowe, John H. et al.; "The Role of Vitrification in Anhydrobiosis"; Annual Review of Physiology; 1998; 60; pp. 73-103.

Gold, David et al.; "A comparative analysis of data generated using two different target preparation methods for hybridization to high-density oligonucleotide microarrays"; Methodology article; BioMed Central; BMC Genomics 2004; 5:2; Jan. 6, 2004; 14pp.

Hammond, Jennifer A. et al.; "Expression Profiling of Glycosyltransferases and Related Enzymes Using Gene Microarrays"; Methods in Enzymology; vol. 416; 2006; pp. 141-156.

Hanash, Samir M. et al.; "Emerging molecular biomarkers-blood-based strategies to detect and monitor cancer"; Nature; Mar. 2011; vol. 8; pp. 142-150.

Hernandez, Gilberto E. et al; "Assessing a novel room-temperature RNA storage medium for compatibility in microarray gene expression analysis"; Short Technical Reports; BioTechniques: The International Journal of Life Science Methods; vol. 47; No. 2; 2009; pp. 667-670.

Hu, Zhibin et al.; "Serum microRNA profiling and breast cancer risk: the use of miR-484/191 as endogenous controls"; Carcinogenesis; vol. 33; No. 4; 2012; pp. 828-834.

Hukins, D.W.L. et al.; "Accelerated aging for testing polymeric biomaterials and medical devices"; Medical Engineering & Physics; 30; 2008; pp. 1270-1274.

Ivanova, Natalia V. et al.; "Protocols for dry DNA storage and shipment at room temperature"; Molecular Ecology Resources; 2013; 13; pp. 890-898.

Jacob, Naduparambil Korah et al.; "Identification of Sensitive Serum microRNA Biomarkers for Radiation Biodosimetry"; PLOS One; Feb. 2013; vol. 8; Iss. 2; 12pp.

Jones, Kathryn L. et al.; "Long-term storage of DNA-free RNA for use in vaccine studies"; BioTechniques; vol. 43; No. 5; 2007; pp. 675-681.

Kingston, Robert E. et al.; "Guanidine Methods for Total RNA Preparation"; Current Protocols in Molecular Biology; 1996; pp. 4.2.1-4.2.9.

Kirschner, Michaela B. et al.; "Haemolysis during Sample Preparation Alters microRNA Content of Plasma"; PLOS One; Sep. 2011; vol. 6; Iss. 9; 9pp.

Krol, Jacek et al.; "The widespread regulation of microRNA biogenesis, function and decay"; Nature Reviews; Genetics; vol. 11; Sep. 2010; pp. 597-610.

Laffont, Benoit et al.; "Activated platelets can deliver mRNA regulatory Ago2•microRNA complexes to endothelial cells via microparticles"; Blood; Jul. 11, 2013; vol. 122; No. 2; pp. 253-261.

Maltezos, George et al.; "Microfluidic blood filtration device"; Biomed Microdevices; 2011; 13; pp. 143-146.

Current Protocols in Molecular Biolog; Chapter 2: Preparation and Analysis of DNA; 2002; 160pp; Ed. John Wiley and Sons, Inc.

Mutter, George L. et al.; "Comparison of frozen and RNALater solid tissue storage methods for use in RNA expression microarrays"; BioMed Central; BMC Genomics; 2004; 5:88; 7pp.

Schmidt, Ulrike et al.; "Therapeutic action of fluoxetine is associated with a reduction in prefrontal cortical miR-1971 expression levels in a mouse model of posttraumatic stress disorder;"Frontiers in Psychiatry; Jul. 10, 2013; vol. 4; Art. 66; 14pp.

Smith, Steve et al.; "Optimal Storage Conditions for Highly Dilute DNA Samples: A Role for Trehalose as a Preserving Agent"; J Forensic Sci; Sep. 2005; vol. 50; No. 5; 8pp.

Tuefferd, Marianne et al.; "Chapter 10: Microarray Profiling of DNA Extracted from FFPE Tissues Using SNP 6.0 Affymetrix Platform"; Formalin-Fixed Paraffin-Embedded Tissues: Methods and Protocols; Methods in Molecular Biology; vol. 724; pp. 147-160.

Wang, Guo-Kun et al.; "Circulating microRNA: a novel potential biomarker for early diagnosis of acute myocardial infarction in humans"; European Heart Journal; 2010; 31; pp. 659-666.

Wang, Kai et al.; "Comparing the MicroRNA Spectrum between Serum and Plasma"; PLOS One; Jul. 2012; vol. 7; Iss. 7; 9pp.

* cited by examiner

INTEGRATED MEMBRANE FOR PRESERVATION OF BIOMOLECULES

CROSS-REFERENCE TO RELATED APPLICATION(S)

This application is a non-provisional patent application claiming priority to U.S. provisional patent application No. 61/685,330 filed on Mar. 14, 2012, entitled "An integrated membrane for the preservation of biomolecules utilizing membrane-adsorbent technology to autonomously fractionate and preserve proteins and nucleic acids for long-term storage at conditions" incorporated by reference herein.

STATEMENT REGARDING FEDERALLY SPONSORED RESEARCH OR DEVELOPMENT

This invention was made under a contract with an agency of the U.S. Government, Army Phase I Contract No: W81XWH-12-C-0002.

FIELD OF THE DISCLOSURE

The present invention relates to an apparatus and method for moiety specific sample extraction from a complex sample matrix in a flow through process. An integrated membrane is used for separation and preservation of biomolecules. Classes of biomolecules, such as those in blood, can be separated and preserved.

BACKGROUND

The present invention relates to separation and analysis of biomolecules, especially those of bodily fluids such as blood. It provides for moiety-specific sample extraction from a complex sample matrix in a flow through process. More particularly, the present invention relates to an integrated membrane for separation and preservation of classes of biomolecules, such as those in blood and other bodily fluids. These separated components are then available to be used for the diagnosis and testing for diseases and other medical conditions.

RELATED ART

Many techniques and devices are available to separate and analyze biomolecules, particularly those biomolecules found in the human body. Present day medical care and treatment focuses on the diagnosis of disease, disfunctions and abnormalities based on the laboratory analysis of bodily fluids, such as blood, using the tools of modern science. Biomolecule sample work-up prior to profiling often requires preservation and the separation into components. Evaluation may be of the various individual components, or groups of components.

Medical testing of a wide variety of different body fluid components is desirable based on developed testing and diagnostic protocols. Such testing and analysis is used to indicate and evaluate various diseases, or other medical conditions. Having the ability to separate and preserve the biomolecules into components for sampling reliably, cost effectively and without contamination enhances the ability to discover and develop new knowledge about diseases, treatments and cures.

Methods for medical and scientific evaluation of components significantly depend on the ability to adequately separate and preserve the components intact, providing pure and uncompromised samples for evaluation based on comparison of healthy and diseased biomolecules. Many techniques and devices are available to make these analyses. The particular ones used will vary with the biomolecule components of concern. These procedures typically require considerable care and attention. The ability to easily collect, separate and analyze biomolecules without risk of contamination is important.

To acquire biomolecules for sampling and analysis is not trivial. For example, the storage of highly labile biomolecules, such as proteins and RNA, requires the use of low (4° C. and −20° C.) and ultra-low (−80° C.) freezers and/or a host of specialized and expensive chemicals to preserve the structural and chemical integrity of the biomolecule. Because of these storage requirements, storing millions of samples to use for early diagnosis is cost prohibitive and impractical. Presently, alternatives to low and ultra-low temperature storage have significant drawbacks.

Evaluation of blood and its components is a particular focus for diagnosis and treatment of many different medical conditions. Human blood comprises a plasma component, and a blood corpuscle component. The blood corpuscle component comprises erythrocytes (i.e., red blood cells), leucocytes (i.e., white blood cells), and blood platelets. The blood plasma component comprises water (90% by volume), dissolved proteins, nucleic acids, glucose, clotting factors, mineral ions, hormones and gases (e.g., carbon dioxide).

Information derived from the analysis of proteins and nucleic acids derived from blood and other fluids and tissues has provided early detection of and diagnosis capability for many medical conditions. For example, analysis of blood proteins and nucleic acids can detect illnesses such as post-traumatic stress disorder (PTSD), traumatic brain injury (TBI) as well as other "hidden" illnesses. The ability to provide early detection and diagnosis facilitates the successful evaluation and treatment of these and other illnesses.

To avoid the stringent demands for low and ultra-low temperature storage required preserve structural and chemical integrity for blood and other fluids, there are preservation methodologies such as those for ribonucleic acid (RNA)/deoxyribonucleic acid (DNA) storage that provide for stabilizing the RNA during collection, processing and storage; however, these technologies are subjectively dependent on the selective ability to extract and purify RNA with minimal exposure to contaminating ribonucleases (RNases). Because RNases are ubiquitous in the clinic and laboratory, clinicians are unable to institutionalize reliable procedures for avoiding contamination.

In an attempt to overcome the inherent problems with RNases contamination, several commercially reagents, such as RNAlater® (Ambion, Austin, Tex.), have been developed to avoid RNases degradation during sample collection, processing and storage. To avoid contamination, these reagents provide for the in situ precipitation of degenerative RNases in cells/living tissues via use of ammonium sulfate. While these reagents theoretically provide for the storage of RNA samples at near room temperature for up to seven (7) days, actual use shows that there is significant mRNA degradation that may occur after three (3) days of near-room temperature storage.

More recently, a new RNA storage reagent trading under the name of RNAstable® (Biomatrica, San Diego, Calif.) was introduced using anhydrobiosis as a method to stabilize and protect biomolecules from degradation at near room temperature. RNAstable® has been shown to store total RNA at near room temperature, and is claimed to do so for up to twelve (12) years according to manufacturer's specifications.

While RNAstable® and other reagents may ultimately provide for longer RNA storage, the use of a reagent generally is highly dependent on the ability to collect, process and, if necessary, purify samples while minimizing any incidence of RNases contamination.

With regard to protein storage, there is currently no commercially available means of storage other than the low and ultra-low temperature methodology. Alternative methodologies exist but are deficient. For example, for blood analysis, alternatives include drying out the sample and adhering it to dried blood spot (DBS) papers or cards (Shleicher & Scheull 903). Current DBS technology is limited and an inferior substitute for low and ultra-low temperature storage of samples. Special training of personnel handling the placement of the blood on the papers/cards is required or large variations and errors can result. For example, DBS papers in use are subject to operator inefficiencies and lack of skill. Operator errors in the distribution of the samples on the matrix is often non-uniform, leading to assay variations (upon recovery). And, samples are recovered using a punch device, which can lead to cross-contamination among samples.

Accordingly, there is a need for an improved method and apparatus for preserving and storing biomolecules. There is an additional need for an improved method and apparatus for long-term storage of biomolecules. There is also a need for an improved method and apparatus for storage of biomolecules at ambient conditions. There is a further need for a method and apparatus that reduces the possibility of sample cross-contamination. There is an additional need for a practical and cost-effective method and apparatus for storing samples. The present invention satisfies these needs and provides other related advantages.

SUMMARY OF THE INVENTION

Targeted extraction is possible with the present invention. It provides moiety-specific sample extraction from a complex sample matrix (such as blood, food, soil, etc.) using a flow through process.

One or more membranes with conjugate parts may be integrated in the apparatus to extract just targeted components. Variations will occur in the sequence of the sorting, which will cause the apparatus to be modified by one of ordinary skill in the art for the apparatus to provide for the best sequence and separation.

It is possible to provide moiety-specific extraction for dry materials also through the use of a buffer. With the present invention, it is possible separate of classes of biomolecules such as cells, proteins and nucleic acids (DNA/RNA) fully preserved from whole blood.

Sample extraction can be done for materials within the cells as well, by using, for example, lysing buffers. The process is performed rapidly. With blood separation, this avoids proteins and RNA degradation.

An integrated membrane illustrated herein provides for preservation of biomolecules, such as proteins and nucleic acids. While the apparatus and method of the present invention are described further for the use of blood-derived biomolecules, the invention is not so restricted and can be used for the preservation generally of biomolecules.

An integrated membrane illustrated herein provides preservation of biomolecules for long-term storage. An integrated membrane illustrated herein provides for storage of biomolecules at ambient conditions.

An integrated membrane illustrated herein provides for rapid separation and processing of samples to avoid degradation.

An integrated membrane illustrated herein provides for separation and preservation of biomolecules without the use of solvents or additives.

An integrated membrane illustrated herein provides one or more membranes with conjugate parts to extract just targeted components.

An integrated membrane illustrated herein provides optimized sequencing and separation of components. By way of example, and not limitation, for nucleic acids, it is necessary to sequence the filtering process to first filter cells, and then proteins to avoid degradation of the nucleic acids.

In an embodiment, an apparatus for preserving biomolecules is provided. The apparatus includes a housing having a matrix portion, and a fluid collection portion disposed within an inner cavity thereof. The housing also includes an aperture permitting access to the inner cavity. A matrix disposed within the matrix portion includes a first layer for collecting substantially all cells from the fluid, a second layer for protein adsorption, and a third layer for nucleic acid adsorption. Fluid enters the housing through the aperture, passes through the matrix, and into the fluid collection portion.

In another embodiment, the apparatus includes a desiccant disposed within the fluid collection portion.

In a further embodiment, the housing of the apparatus includes a barrier disposed between the matrix portion and the fluid collection portion.

In an additional embodiment, the barrier includes openings through which fluids passes from the matrix portion to the fluid collection portion.

In yet another embodiment, the housing of the apparatus includes a locking mechanism for engaging a syringe.

In yet a further embodiment, the aperture is disposed on a distal end of a neck extending away from the housing.

In an embodiment, each layer comprises a fluid permeable membrane.

In another embodiment, each layer comprises a membrane held within a holder.

In a further embodiment, each membrane is disposed between upper and lower portions of the holder.

In an additional embodiment, each holder removably engages at least one adjacent holder.

In yet another embodiment, at least the nucleic acid adsorption layer is separable from the matrix.

In yet a further embodiment, at least the nucleic acid adsorption layer includes at least one line of weakness defining a plurality of removable sections.

In an embodiment, a method for preserving biomolecules is provided. The method includes passing fluid through a matrix; collecting substantially all cells from the fluid in a layer of the matrix; adsorbing protein from the fluid in a layer of the matrix; and adsorbing nucleic acid from the fluid in a layer of the matrix.

In another embodiment, the method includes drying the fluid that has passed through the matrix.

In a further embodiment, the method includes drying at least the nucleic acid adsorbing layer.

In an additional embodiment, the method includes separating the matrix from the fluid that has passed through the matrix.

In yet a further embodiment, the method includes containing the matrix within a housing.

In yet another embodiment, the method includes injecting the fluid into the housing using a syringe matingly engaged with the housing.

In an embodiment, the method includes containing each layer within a holder.

In another embodiment, the method includes separating at least the nucleic acid adsorbing layer.

In an additional embodiment, the method includes defining at least the nucleic acid adsorbing layer into separate removable sections.

In an embodiment, a system for preserving biomolecules is provide. The system includes a housing containing a matrix therein. The matrix includes a first layer for collecting substantially all cells from the fluid, a second layer for protein adsorption, and a third layer for nucleic acid adsorption. The system also includes a storage case for containing at least the third layer after separation from the matrix.

In a further embodiment, an apparatus for preserving biomolecules is provided. The apparatus includes a housing comprising a matrix portion, and a fluid collection portion disposed within an inner cavity thereof; wherein the housing includes an aperture permitting access to the inner cavity. The apparatus also includes a matrix disposed within the matrix portion, comprising an asymmetric layer for filtering material from the fluid. Fluid enters the housing through the aperture, passes through the matrix, and into the fluid collection portion.

In another embodiment of the apparatus, the matrix further includes a layer for adsorption of a first component of the material.

In an additional embodiment of the apparatus, the matrix further includes a layer for adsorption of a second component of the material.

This brief summary has been provided so that the nature of the invention may be understood quickly. A more complete understanding of the invention can be obtained by reference to the following detailed description of the preferred embodiments thereof concerning the attached drawings.

BRIEF DESCRIPTION OF THE DRAWINGS

The various present embodiments now will be discussed in detail with an emphasis on highlighting the advantageous features with reference to the drawings of various embodiments. The illustrated embodiments are intended to illustrate, but not to limit the invention. These drawings include the following figures, in which like numerals indicate like parts.

DETAILED DESCRIPTION

Figure 1:
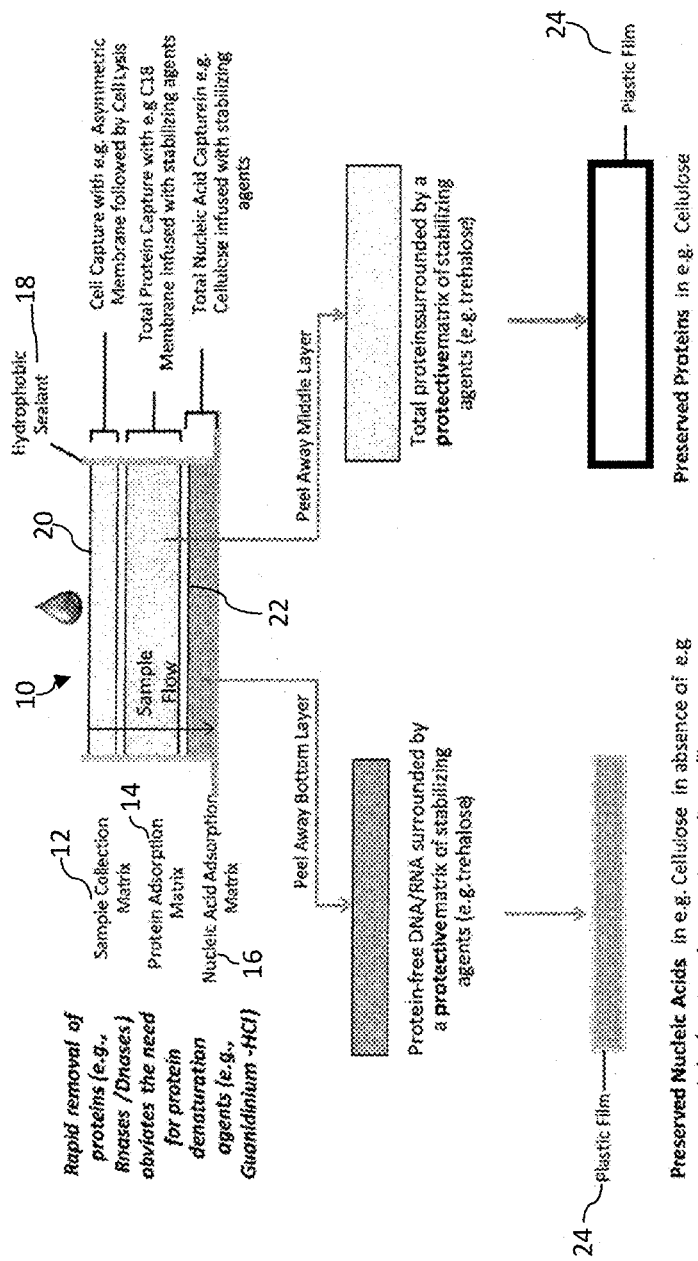
FIG. 1 is a diagram of an integrated membrane illustrating an embodiment of the present invention.

The following detailed description describes the present embodiments with reference to the drawings. In the drawings, reference numbers label elements of the present embodiments. These reference numbers are reproduced below in connection with the discussion of the corresponding drawing features.

The term "fluid" used in the specification refers to, but is not limited to, bodily fluids, such as blood in its original composition, partially fractionated blood, blood plasma, and the like.

The terms "corpuscle" or "cell" used in the specification refer to, but are not limited to erythrocytes, leucocytes, blood platelets and the like.

The term "biomolecule" used in the specification refers to, but is not limited to, a molecule produced by living cells (e.g., protein, carbohydrate, lipid, or nucleic acid).

The term "nucleic acid" used in the specification refers to, but is not limited to, ribonucleic acid, deoxyribonucleic acid and the like.

As shown in FIGS. 1 to 13 for purposes of illustration, various embodiments of the present invention incorporate an integrated membrane assembly for the preservation of biomolecules that utilizes membrane-adsorbent technology to autonomously fractionate and preserve components, including, but not limited to, proteins and nucleic acids for long-term storage at ambient conditions.

The integrated membrane avoids the possibility of rapid degeneration of biomolecules such as highly labile macromolecules. The technology allows the user to apply a sample (e.g., blood) directly on a multi-layer membrane wherein nucleic material is extracted, purified and preserved in one rapid step. Samples are passed through the integrated membrane in a flow-through process. For example, blood is drawn with the syringe or other blood collection device and, after blood draw (e.g., ~50-500 μl), the blood is dispensed across the integrated membrane and the processing occurs automatically. A preferred maximum volume for whole blood draw is 500 μl to reduce the possibility the integrated membrane being clogged with cells.

The integrated membrane provides: (1) rapid, on-site collection of samples, such as nucleic material (e.g., RNA, DNA); and (2) autonomous collection of samples, precluding any variations due to operator error. A benefit of rapid, on-site collection is, that prolonged exposure to contaminants is reduced. For example, with blood, for collection of nucleic material, prolonged exposure to contaminants such as RNases/DNases is minimized. A benefit to autonomous collection of RNA/DNA is that the potential for variations due to operator error is eliminated. The integrated membrane obviates the need for the use of protein denaturants, which are typically used during the sampling process, to inactivate RNases/DNases, which provides for the use of unaltered use of the RNA/DNA. This provides for recovery of the RNA/DNA from the integrated membrane using a standard RNA/DNA suspension buffer (e.g., a nuclease free TE buffer) without the need to remove protein denaturants (necessary for inactivation of the RNases/DNases) prior to analysis. Avoiding the use of protein denaturants is desirable, as the removal of protein denaturants typically requires the use of toxic reagents (e.g., phenol/chloroform) that can cause significant loss of RNA/DNA. Thus, eliminating the use of protein denaturants saves time, reduces expense, and increases RNA/DNA yield.

An integrated membrane embodying the present invention overcomes limitations of current DBS technology and other technologies by enabling autonomous collection. For example, collection of proteins from whole blood using the present invention avoids inaccuracies and variations in results. The integrated membrane also can incorporate a rapid drying process. For proteins in blood samples, this enables the proteins to be uniformly distributed in the matrix thus reducing any sources of assay variations. The membrane or membranes selected are dependent upon the sample and the particular separation and preservation sought. For example, if the membrane selected has a high binding capacity, the integrated membrane can be sufficiently small enough to make the use of a punch device upon recovery unnecessary. To elute/recover proteins, the integrated membrane can be designed to provide for incubation and/or washing in an organic solvent (e.g., a physiological buffer with hydrophobic elution solvents and low salt (e.g., lucine)). The integrated membrane may also be used in conjunction with a solvent that extracts proteins from cells without denaturing the proteins; as such, the proteins are captured in their native states within the protein adsorption matrix.

As shown in FIG. 1, in one preferred embodiment there is an integrated membrane assembly 10 comprises a matrix having one or more distinct layers stacked and mechanically pressed (i.e., sandwiched) together as a single unit. The sides of the assembly 10 are sealed with a hydrophobic sealant (e.g., wax coating, wax paper or the like) 18 to provide directional flow of the blood sample/solvent mixture through all the layers of the integrated membrane assembly 10. Each layer comprises a porous membrane and has its own function. Each membrane may be made from various materials including, but not limited to, cellulose. The assembly is held within a container (not shown). The sides of the assembly 10 are the only regions confined by the hydrophobic sealant thereby preventing fluid creep around the sides of the integrated membrane assembly 10. The top or upstream side 20 and bottom or downstream side 22 are not sealed and are exposed to the fluid. The top side 20 is exposed to whole blood while the bottom side 22 is exposed to the flow-through processed sample.

The assembly 10 comprises a sample collection layer 12 (alternatively referred to as a cell collection layer), a protein adsorption layer 14, and a highly adsorbent nucleic material (e.g., RNA/DNA) preservation layer 16. In the sample collection layer 12, cells from whole blood or tissues are captured and subsequently lysed in the presence of a nucleic acid/protein extraction buffer such as e.g., 0.8 M guanidine hydrochloride, 0.1% triton X-100. The sample collection layer 12 comprises an asymmetric membrane that has varying pore size (large to small) across the flow direction of the sample. An example of an asymmetric membrane is a VIVID Plasma Separation Membrane (Pall Corporation, Port Washington, N.Y.). The protein adsorption layer 14 selectively captures and stabilizes proteins from cell extracts immediately upon lysis. In this manner, the protein adsorption matrix protects the RNA/DNA from RNA/DNA-degrading enzymes (e.g., RNases/DNases). The protein adsorption layer 14 may be made from cellulose linked with C18 polymeric chains. Stearic acid and octadecanoic acid are the most common fatty acids found in nature and also constitute the functional part of the most common reverse phase resin, C18, used to as part of the protein adsorption layer 14. The RNA/DNA preservation layer 16 stabilizes the RNA/DNA using a bio-inspired reagent (e.g., trehalose) that protects biomolecules in a dry state. The preservation layer 16 may be cellulose-based, and infused with trehalose to minimize oxidative stress and promote stability. Alternatives to trehalose include rapid freezing. Pore size in the preservation layer 16 ranges between one hundred (100) to four hundred (400) nanometers to one (1) angstrom.

The sample collection layer 12, protein adsorption layer 14 and the RNA/DNA preservation layer 16 are subsequently peeled away manually (e.g., by hand, with or without the use of tweezers), dried and stored. Alternatively, the layers 12, 14, 16 may be dried while still a single unit and subsequently separated from one another prior to storage. In another alternative, the assembly 10 may be stored intact after being dried. The layer(s) may be stored in various containers including a storage case having separate compartments/recesses for each layer, moisture-barrier pouches with desiccants (e.g., salts, swellable silica) or the like for long-term storage at ambient temperature. The integrated membrane assembly 10 can be used in conjunction with a solvent (e.g., 0.8 M guanidine hydrochloride, 0.1% triton X-100) that serves to extract, purify and preserve the proteins and nucleic acids in individual layers within the assembly 10.

In one preferred embodiment designed for use with blood separation and preservation, the assembly 10 eliminates the need to pre-process the blood sample, as whole blood is directly applied to the sample collection layer 12. Once applied to the sample collection layer 12, the solvent (e.g., 0.8 M guanidine hydrochloride, 0.1% triton X-100) is added to lyse the cells enabling the lysate (containing intracellular proteins/DNA/RNA) to flow through the matrix and into the protein adsorption matrix 14 where proteins (e.g., nucleases) are retained. The lysis buffer breaks open the blood cells and releases the cellular content (e.g., proteins and nucleic acids). The asymmetric membrane of the sample collection layer 12 traps and filters out cellular debris, followed by the protein adsorption layer 14 (i.e., the C18 conjugated cellulose membrane) which selectively adsorbs all proteinacious material as it is highly hydrophobic. Finally, the highly hydrophilic RNA/DNA preservation layer 16 (e.g., a cellulose membrane infused with trehalose) adsorbs and stabilizes all nucleic acids. The immediate removal of proteins (e.g., nucleases) from the lysate provides a mechanism for protecting the RNA/DNA from degradation. Moreover, it avoids the need for protein denaturation agents (e.g., Guanidinium HCl) to inactivate RNases/DNases.

Protein denaturation agents are likely to interfere with downstream applications/reactions, such as quantitative polymerase chain reaction (PCR). Therefore, the absence of these reagents will enable a user (e.g., a researcher, lab technician, physician or the like) to directly use the protein and/or RNA/DNA upon elution from the matrix. As the RNA/DNA can be stored in the matrix without any protein contaminants, the RNA/DNA is not likely to degrade upon elution of the sample from the matrix. The integrated membrane assembly 10 avoids the use of protein denaturants (e.g., Guanidine-HCl) to inactivate RNases/DNases, as proteins are immediately separated from the RNA/DNA upon cell lysis. Because protein denaturants are unnecessary, the user is able to (1) capture proteins in their native states within the protein adsorption matrix and (2) use the RNA/DNA directly, upon elution from the matrix, without the need to remove the protein denaturants. The avoidance of protein denaturants is advantageous as protein denaturants are known to interfere with most downstream applications, such as PCR.

The integrated membrane assembly 10 of the present invention provides a seamless process. In a preferred embodiment, a first stage is the sample collection layer 12 that enables the autonomous collection of whole cells (as well as damaged cells) from the blood sample within the integrated membrane assembly 10. The sample collection layer 12 (stage 1) is designed to capture intact cells from whole blood such that cells are lysed only upon addition of the cell lysis buffer. The buffer may be pre-loaded into the syringe prior to blood draw so that upon blood draw, the buffer mixes in with the blood sample and starts the lysis process. Alternatively, the buffer may be introduced to the integrated membrane assembly 10 after the blood sample is applied to the upstream side 20 of the integrated membrane assembly 10. In either case, blood cells are collected in the membrane intact thus preventing the release of intracellular RNases/DNases prior to the addition of cell lysis buffer. The sample collection layer 12 all cellular debris, including the membranes of ruptured/damaged cells. The sample collection layer 12 may be discarded if a user is only interested in nucleic acids. Some users may want to analyze the cellular debris and look for membranes—which is also possible by eluting out the cellular debris from the top membrane (i.e., the sample collection layer 12).

The sample collection layer 12 comprises an asymmetric membrane with a minimum pore size of 0.2 µm. Asymmetric membranes differ from symmetric micro-porous membranes in that an asymmetric membrane comprises larger pores on an upstream portion of the membrane and smaller pores on a downstream portion of the membrane. The larger upstream pores act as a pre-filter while the smaller downstream pores act as an absolute cut-off layer or exclusion zone. Accordingly, the asymmetric membrane is able to efficiently capture a larger number of cells, as compared to conventional micro-porous membranes, while also reducing the possibility of clogging on the upstream side of the membrane. Moreover, the asymmetric membrane captures erythrocytes, which are able to traverse the narrowest blood vessel.

Once the cells in the blood sample have been collected by sample collection layer 12, in a second stage, the protein adsorption layer 14 extracts proteins followed by a third stage where the RNA/DNA is extracted and purified (in preparation for long-term preservation at ambient temperature) from the blood sample. After the blood cells are collected in the sample collection layer 12, the captured cells are lysed using a cell lysis buffer. The cell lysates then enter the protein adsorption layer 14 immediately upon lysis. The purpose of the protein adsorption layer 14 is to selectively deplete proteins from the lysates such that the nucleic acids are preserved in a protein-free environment in the RNA/DNA adsorption layer 16. The protein adsorption layer 14 comprises a membrane conjugated to an 18-mer hydrocarbon chain (C18) wherein proteins are selectively adsorbed from the solution via high-affinity binding to non-polar residues. The protein adsorption layer 14 enables hydrophilic molecules, such as RNA/DNA, to flow through the layer 14 for subsequent preservation of protein-free nucleic acids in the RNA/DNA adsorption layer 16.

Once the cell lysates have passed through the protein adsorption layer 14, the protein-free RNA/DNA can be captured in the highly adsorbent nucleic acid capture layer (i.e., the RNA/DNA adsorption layer 16). The RNA/DNA adsorption layer 16 comprises a cellulose membrane infused with any hydrobiotic and/or stabilizing agents (e.g., trehalose).

As outlined above, the layers 12, 14, 16 are stacked and pressed together as a single unit and sealed with the hydrophobic coating 18 to provide directional flow of the blood sample/solvent mixture through all the layers 12, 14, 16. Once the lysates have flowed through the integrated membrane assembly 10, the protein and nucleic acid adsorption layers 14, 16 are peeled away from the sample collection layer 12, air dried and stored in an opaque, moisture-barrier container (not shown) (e.g., a case, pouch, or the like) so that the layers 14, 16 are protected from light and moisture for long-term storage in ambient conditions. The term "peeled away" is used only in the sense that layers 12, 14, 16 are pressed together to form the integrated membrane assembly 10, and the layers 12, 14, 16 may stick to each other due to the presence of lingering moisture from the sample/buffer or from the layers 12, 14, 16 adhering to each after having dried. The container may also include desiccants for moisture control. If necessary, the adsorption layers 14, 16 can be encased in a plastic film 24 prior to storage in the container.

The cell lysis buffer/solvent can have a dual functionality in that it may acts as both a cell lysis buffer and a liquid medium that facilitates selective adsorption of protein contaminants. To achieve efficient cell lysis, the solvent comprises a non-ionic surfactant, such as Triton X-100, to solubilize proteins and lipids. Triton X-100 helps bind proteins to the protein adsorption layer 14. A concentration of 0.1% Triton X-100 in the membrane of the protein adsorption layer 14 enhances protein binding to the layer 14 without adversely affecting red/white blood cell lysis. The buffer further comprises 20 mM Tris-HCl (pH 7.5), 150 mM NaCl, 1 mM Na2EDTA, 1 mM EGTA and protease inhibitors.

Figure 2:
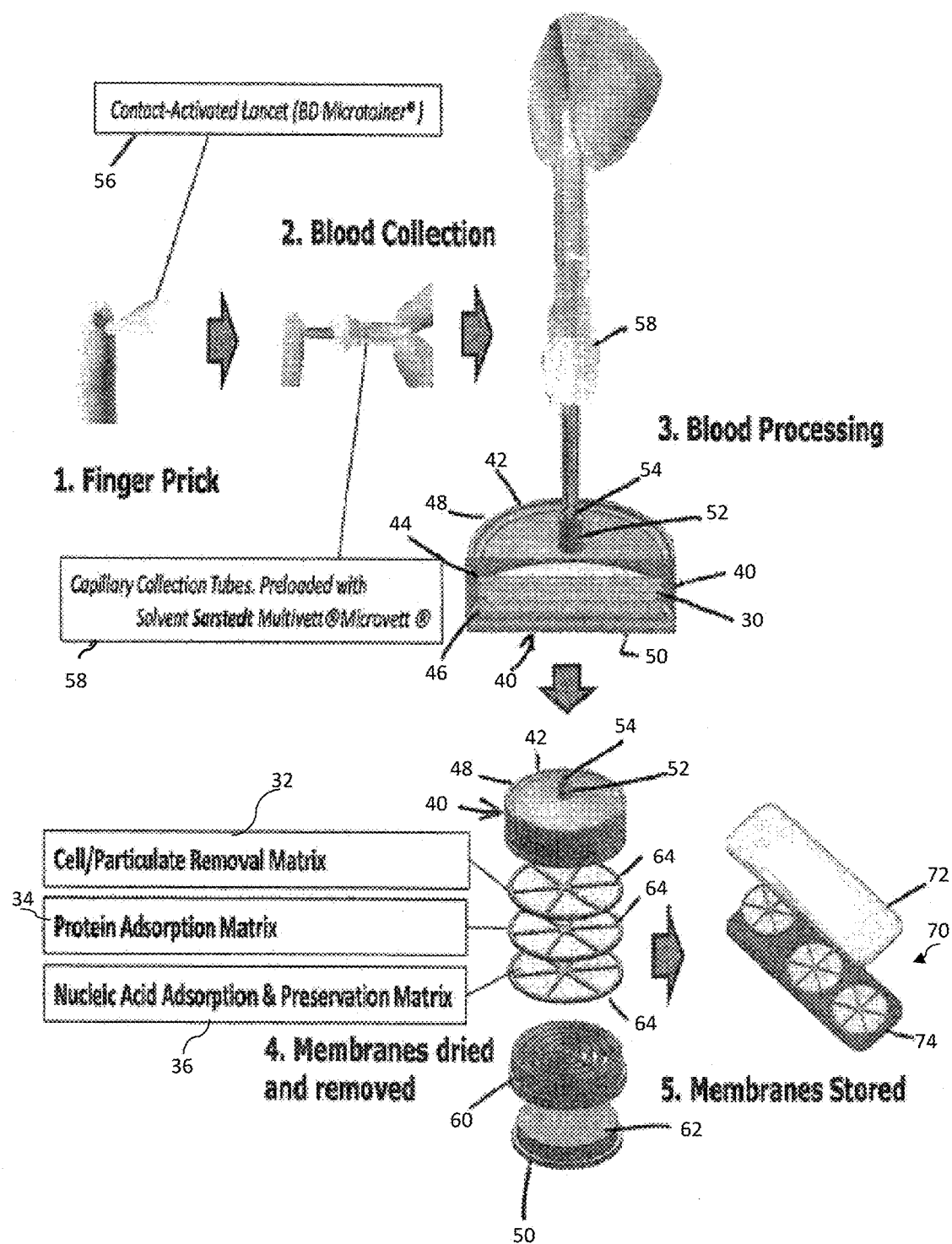
FIG. 2 illustrates another embodiment of the present invention.

In another preferred embodiment, as shown in FIG. 2, an integrated membrane assembly 30, similar to the assembly 10, is disposed within a canister assembly 40 for preserving biomolecules. The assembly 40 comprises a housing 42. An inner cavity of the housing 42 is defined by a portion 44 in which the integrated membrane assembly 30 is disposed (alternatively referred to as the matrix chamber) and by a portion 46 in which fluid is collected (alternatively referred to as the fluid collection chamber). The housing 42 includes generally cylindrical cover portion 48 (generally U-shaped in cross-section) and a bottom portion 50. Other shapes may work equally as well. The cover portion 48 includes a neck 52 extending away from the housing 42. An aperture 54 permitting access to the inner cavity of the housing 42 is disposed on a distal end of the neck 52. A cap, cover or other seal may be disposed over the aperture 54 prior to use. In use, if the sample to be separated and/or preserved is blood, a blood sample may be obtained by finger prick using a contact-activated lancet 56. Alternatively, if a much larger sized blood sample is desired, a syringe with a hypodermic needle may be used to draw blood. Blood is collected from the finger using a capillary collection tube pre-loaded with solvent 58 (e.g., 0.8 M guanidine hydrochloride, 0.1% triton X-100). The end of the capillary collection tube may be placed within the aperture 54 of the neck 52 and the blood/solvent mixture injected into the housing 42. Once the blood/solvent mixture enters the housing 42 through the aperture 54, passes through the assembly 30, and into the fluid collection portion 46. The assembly 30 comprises a sample collection layer 32 (alternatively referred to as a cell collection layer), a protein adsorption layer 34, and a highly adsorbent RNA/DNA preservation layer 36 (alternatively described as the RNA/DNA adsorption layer). In the sample collection layer 32, substantially all cells from whole blood or tissues are captured and subsequently lysed in the presence of a nucleic acid/protein extraction buffer. The sample collection layer 32 comprises an asymmetric membrane that has varying pore size (large to small) across the flow direction of the sample. A generally cylindrical insert 60 (generally U-shaped in cross-section) is partially disposed within the inner cavity to define the portions 44, 46 of the housing 42, and creating a permeable barrier therebetween. A top side of the insert 60 includes a grill comprising a series of concentric rings defining arcuate spaces between the rings through which fluid and gases can pass. The insert 60 press-fits within the cover portion 48. Sidewalls of the cover portion 48 press-fit engage sides of the insert 60, and an annular portion of the insert 60 engages the bottom of the sidewalls of the cover portion 48. A desiccant 62 is disposed within the fluid collection portion 46 for drying any fluid passing through the barrier from the integrated membrane assembly 30. The bottom of the insert 60 engages the bottom portion 50 of the housing 42 to contain the desiccant and any fluids within the fluid collection portion 46 of the housing 42. The modular structure of the canister assembly 40 allows for rapid and easy separation of the extracted and stabilized nucleic acid species in the sample from the cellular, protein, enzymes, processing reagents and other contaminants.

The layers 32, 34, 36 may be in the form of fluid-permeable cellulose membranes such as those discussed above with respect to assembly 10. Silica membranes are an alternative membrane for nucleic acid capture due to their strong nucleic acid binding capacity, facile and high recovery, rapid drying, and buffer compatibility properties. Like a hydrophilic cellulose membrane infused with trehalose, Silica ($SiO_2$) is positively charged and forms an electrostatics connection to the phosphate backbone of the nucleic acid. Silica matrices are the most popular solid phase support for binding nucleic acids due to their quick and efficient purification procedures. DNA and RNA bind to silica matrices with high affinity due to their negatively charged phosphate backbone and the positively charged silica particles (silicon oxide). Silica membranes used as an alternative to cellulose membranes, including, but not limited to, for any one or more of the layers 32, 34, 36 will have the porous structure described with respect to the layers 32, 34, 36. The basic scientific method is a well-established as it has been implemented in a number of blood DNA extraction techniques. The main limitation of this technique in traditional laboratory process is the relatively high protein contamination present in a sample. However, the integrated membrane assembly 30 can circumvent this limitation by having a protein pre-filter step prior to nucleic acid binding, thereby leading to a greater purity in the overall process.

Based on the silica matrix surface and binding buffers, silica gels can be selectively tailored for capturing and eluting specific nucleic acid species. Silica gels have a high binding capacity of up to 1 µg of nucleic acid per 10-3 cubic centimeters. Since blood has about 0.5 µg/µl of nucleic acids, a volume of 0.3 cc of silica matrix is sufficient to extract all nucleic acid species present in 500 µl of whole blood. All parameters of the silica membrane are being optimized for greater than 99% capture of all nucleic acid in a sample as well as species-specific elution.

A commercially available desiccant may be used (e.g., Ecopack Clay Desiccant, Inter Dry Moisture Control). This material combines the moisture absorption property of calcium chloride with the ruggedness of clay to render a single use desiccant capable of rapidly removing enough water for 70% of its own weight 21. The increased hygroscopy relative to silica gel (7× more) enable the rapid drying of the nucleic acid carrying membrane 36.

Each layer 32, 34, 36 comprises a membrane held within a holder 64 where the membrane is sandwiched between upper and lower portions 66, 68 of the holder 64. Each portion 66, 68 includes an upwardly extending annular ring capable of engaging an annular recess on the bottom side of an above adjacent portion 66, 68. This allows the membrane to be held firmly between the portions 66, 68. This also allows the upper portion 66 of the holder 64 for layer 34 to engage the bottom portion 68 of the adjacent holder 64 for layer 32. Likewise, this further also the lower portion 68 of the holder 64 for layer 34 to engage the upper portion 66 of the adjacent holder 64 for layer 36. In this manner, each holder 64 is capable of removably engaging at least one adjacent holder 64.

Figure 3:
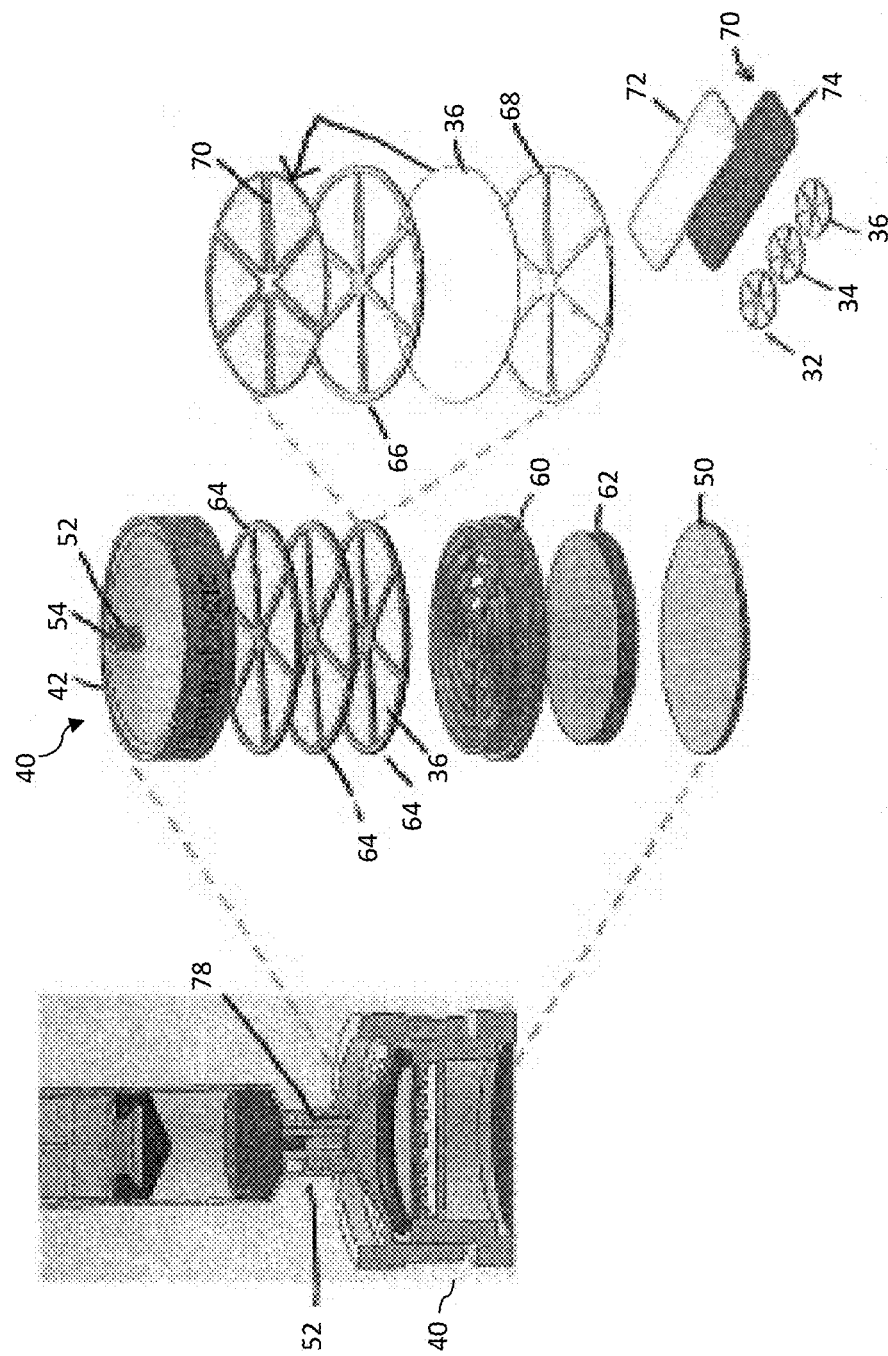
FIG. 3 illustrates a further embodiment of the present invention.

Each layer 32, 34, 36 may include at least one line of weakness 70 (e.g., perforations or slits in the membrane) defining a plurality of removable sections or segments (FIG. 3 shows an exploded view of layer 36 with an intact membrane 36 between top and bottom portions of the holder 64). This pie-shaped design of the membrane 32, 34, 36 allows a user to easily separate sections of each of the membrane 32, 34, 36 for easy partial sample analysis, leaving other sections of the membrane available for analysis at a later time or for concurrent analysis. The pie-shaped design of the silica membrane used for nucleic acid separation allows partial sample analysis without affecting the entire sample. This pie-shaped design prevents sample destruction from the extract/preserve cycle that conventional sample storage methods currently suffer from.

A fluid-impermeable gasket (e.g., silicone, rubber) may be disposed between adjacent layers 32, 34, 36 to provide directional flow of the blood sample/solvent mixture through all the layers 32, 34, 36 of the integrated membrane assembly 30 and prevent the blood-sample/solvent mixture from moving between the layers 32, 34, 36 and the sidewall of the inner cavity of the housing 42.

The canister assembly 40 and the holders 64 are re-usable after being sterilized. Although the canister assembly 40 and holders 64 are illustrated as being circular in cross-section, they are not limited to that shape. The canister assembly 40 and holders 64 may be come in various polygonal cross-sectional shapes including, but not limited to, triangular, square, rectangular, pentagonal, hexagonal, heptagonal, octagonal or the like. The desiccant may be discarded after each use.

A storage case 70 may be used to store the membranes of each layer 32, 34, 36 after they have been removed from their respective holders 64. Alternatively, the membranes for layers 32, 34 containing cellular debris and proteins may be discarded while only the membrane for layer 36 containing nucleic material is storage. The storage case 70 includes upper and lower portions 72, 74 that matingly engage using a press-fit or other known conventional methods. One or more recesses (not shown) may be formed in an upper surface of the lower portion 72 in which the membranes to be stored may be disposed and kept separate from one another. For example, the upper surface of the lower portion 72 may include three recesses (i.e., one recess per membrane so that the membrane of each layer 32, 34, 36 from a particular sample may be stored.

FIG. 3 illustrates an embodiment substantially similar to the embodiment illustrated in FIG. 2, except that FIG. 3 illustrates an embodiment where a syringe matingly engages the canister assembly 40. A conventional syringe 76 comprises a plunger that fits tightly in a cylindrical tube. The plunger can be pulled and pushed along inside the tube, allowing the syringe to take in and expel a liquid or gas through an orifice at the open end of the tube. The open end of the syringe 76 may be fitted with a hypodermic needle. In the instant application, the syringe 76 is used to draw blood, and subsequently inject the blood into the canister assembly 40 through the aperture 54. The hypodermic needle is attached to the syringe using a locking mechanism. A syringe typically includes a male fitting, and the needle includes a female fitting, which engages the male fitting on the syringe to provide a leak-free connection between the male and female fittings. The male and female fittings may engage in various ways including, but not limited to, a tabbed hub on the female fitting which screws into threads in a sleeve on the male fitting, the male and female fittings being pressed together and held by friction, etc. The syringe and hypodermic needle may be connected using various other conventional locking methods. As seen in FIG. 3, the neck 52 includes female fittings 78 same as/similar to those found on a hypodermic needle for engaging the male fittings on the syringe 76.

As shown in FIGS. 2 and 3, the nucleic acids adsorbed onto the silica gel-based matrix can be manually removed from the canister assembly 40. Furthermore, the nucleic acids extracted are stored in separate pie-shaped matrix subcomponents that allows for easy sample aliquots without exposing the entire sample to the extraction process. Traditionally, in order to process a portion of a sample, the entire sample must be extracted/thawed from its preserved state— followed by re-processing/freezing of the unused portion. This extraction/preservation (thaw/freeze) cycle is known for many components to damage the integrity of the sample. The built-in aliquots avoid the extraction/re-preservation— enabling the long-term preservation of components, for example, the nucleic acid sample. Furthermore, the present invention maximizes the speed of tissue processing. Increased processing speed not only reduces risk/cost from tissue handling but also is critical for removing the sample, such as DNA/RNA, from components that can denature it or otherwise compromise its integrity.

In order to ensure both patient safety and optimal function, all the components of the canister assembly 40 are sterilized. A labile molecule such as RNA requires the utmost care in handling, which includes ensuring that there is no RNases contamination. Starting with fabrication, all elements and materials acquired for the canister assembly 40 are made under good manufacturing practice (GMP) with proper sterilizing techniques used for each element (autoclave, gamma irradiation, e-beam). Ensuring that the sample remains as sterile as possible, all canister assemblies 40 are individually wrapped when shipped from the factory. The principals applied in the instant specification allow extracted sterile nucleic acids stored at room temperature under dry conditions to remain intact for at least 5 years if not much more.

A system (not shown) may comprise a canister assembly, and a storage case. The canister assembly and storage case are same as/similar to those described above.

Prototypes and Testing on Blood

Figure 4:
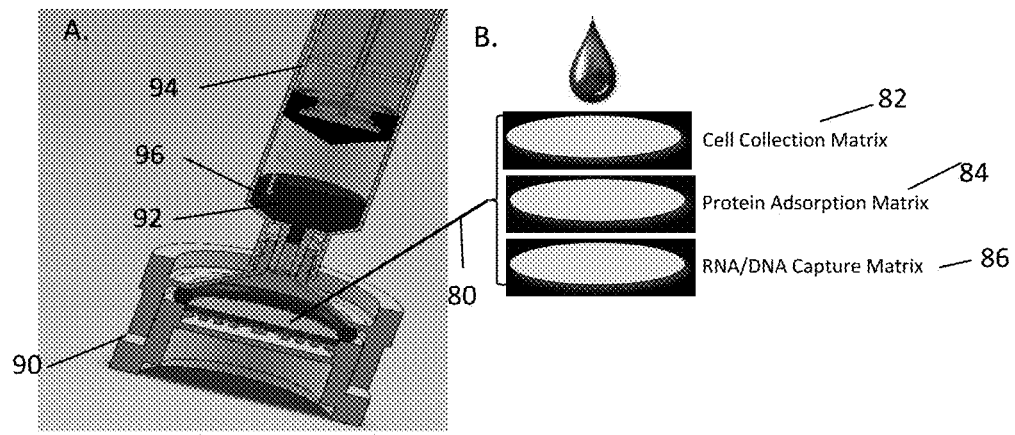
FIG. 4 illustrates a prototype device in accordance with an embodiment of the present invention.

The present invention is directed to rapidly extracting components, such as nucleic acid species from complex body tissue (e.g., whole blood) through a moiety specific sorting process that separates tissue constituents by type of biological molecule. A device embodying the present invention comprises an integrated membrane composed of distinct matrices designed to autonomously extract, purify and preserve the intended sample, such as RNA/DNA. Preferably it may also contain a low-cost, sterile syringe/capillary sample collector pre-loaded with solvent. As shown in FIG. 4, a prototype integrated membrane assembly 80 was constructed comprising three distinct matrices or membranes pressed together as a single unit. The assembly 80 included a cell collection layer 82 comprising an asymmetric membrane wherein blood cells from volumes as little as 5 μl to as large as 50 μl whole blood were collected prior to lysis (size sorting). The porosity of the membrane was carefully selected in order to trap and remove cell/cellular debris while allowing nucleic acid species and proteins to flow through. The assembly 80 also included a protein adsorption layer 84 designed to selectively remove proteins from the cell free flow through. The protein adsorption layer 84 comprises a regenerated silica membrane conjugated to an 18-mer hydrocarbon chain (C18) wherein proteins were selectively adsorbed from solution through the binding of non-polar amino acid residues to the hydrophobic resin. The nucleic acid species remaining in the sample flow through were stabilized and preserved in the RNA/DNA adsorption layer 86. The assembly 80 was housed in a sample extraction canister 90. Upon use, blood/tissue 92 was drawn into a syringe/capillary sample collector 94 pre-loaded with solvent 96 (same/similar to the solvent disclosed above) and dispensed into the housing 90 whereby RNA/DNA was extracted and preserved in a nuclease-free environment.

The initial design for the cell collection layer 82 comprised a cellulose membrane impregnated with a compound (e.g., trehalose) that stabilizes RNA/DNA in the dry state. The membrane for capturing cells from whole blood without inducing cell lysis during the collection process in layer 82 was adapted from a BTS Asymmetric Membrane (Pall Corporation). The membrane for separating nucleases and other degradative enzymes from the extracted RNA/DNA in layer 84 was adapted from an Empore™ Disk, C18 (3M Corporation). The membrane for Stores RNA/DNA in a dry format in layer 86 was adapted from Whatman® Cellulose Chromatography Paper Grade 3MM (GE Healthcare).

Figure 5:
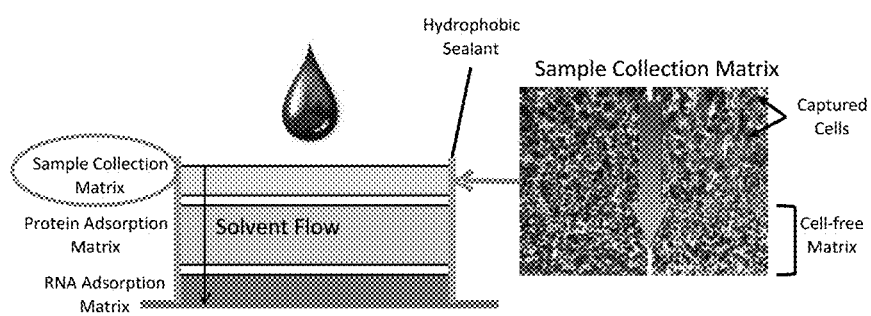
FIG. 5 illustrates the function and structure of an asymmetric membrane of a sample collection layer or matrix in accordance with an embodiment of the present invention.

FIG. 5 illustrates the function of the asymmetric membrane of a sample collection layer or matrix. The sample collection matrix (stage one of, for example, a three stage process) is designed to capture intact cells from whole blood such that cells are lysed only upon addition of the solvent (e.g., 0.8 M guanidine hydrochloride, 0.1% triton X-100). The cells are collected in the membrane intact thus preventing the release of intracellular RNases/DNases prior to the addition of the solvent.

It should be noted that a user may not prefer to lyse the cells. This can occur in a situation where the user wants to capture only the freely circulating RNA/DNA—such as from some cancers, viruses, etc. In this case, because the user does not want RNA/DNA from inside the cells, the user has to be extremely careful not to rupture the cells. So, the user captures it (without crushing the cells) with the asymmetric membrane 12. Therefore, a lysing buffer is used only in those situations when a user wishes to capture RNA/DNA present inside the cells. The choice is up to the user/ application.

As discussed previously, the integrated membrane performs a seamless process; in a preferred embodiment it may be a three stage process, but more or less stages may be optimum depending on the sample to be gathered, separated and/or preserved. For a three stage process, the first stage is typically a sample collection matrix that enables the autonomous collection of whole cells within the integrated membrane (FIG. 5). To enable autonomous sample collection, the sample collection matrix may meet the following requirements: (1) enable the collection of all the cells in the sample such that all cells are capable of being lysed in the matrix prior to entering the protein adsorption matrix; and (2) prevent premature cell lysis if the user would like to specifically isolate non-cellular nucleic acids—such as from pathogens or other circulating DNA/RNA. Cells are lysed in the sample collection matrix only upon addition of the solvent (e.g., 0.8 M guanidine hydrochloride, 0.1% triton X-100), which acts to lyse the cells while inactivating intracellular RNases/DNases. Again, it should be noted that lysing can be done at any point that a user wishes to (e.g., in the syringe when fluid containing nucleic acids (e.g., blood) mixes with solvent pre-loaded into the syringe, in the sample collection membrane after the user has previously placed fluid containing nucleic acids on the sample collection membrane, etc.). Whole blood contains $5 \times 10^6$ erythrocytes and $1 \times 10^4$ leukocytes per micro liter.

In a preferred embodiment, the membrane may be asymmetrical. Due to its unique design, an asymmetric membrane separates a large number of blood cells using a single 25 mm disk. Moreover, the asymmetric membrane is able to separate erythrocytes that are able to traverse the narrowest blood vessel—a feature that have made these cells difficult to capture using conventional symmetric microporous membranes. Asymmetric membranes differ from conventionally cast symmetric microporous membranes in that the larger pores upstream act as a pre-filter while the smaller pores downstream act as an absolute cut-off layer or exclusion zone. As such, the asymmetric membrane is able to efficiently capture a larger number of cells, as compared to conventional symmetric microporous membranes.

Figure 6:
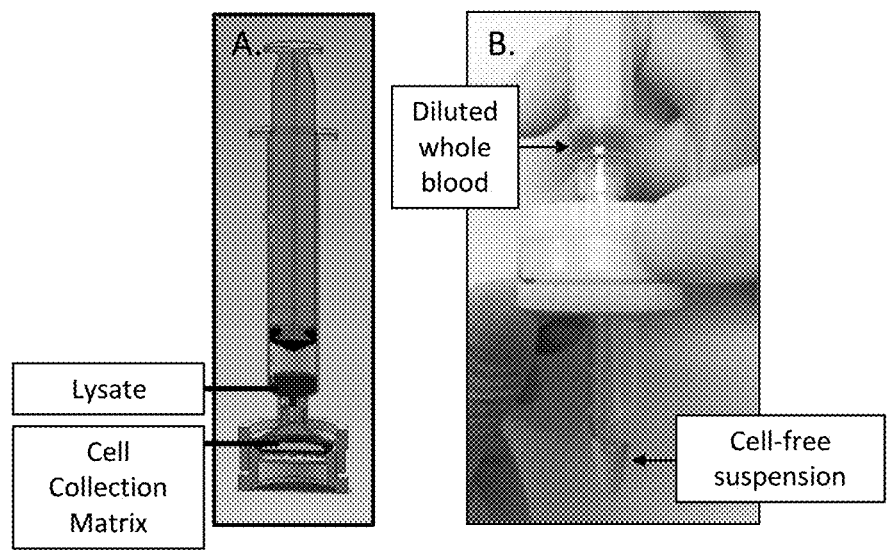
FIG. 6 illustrates another prototype device in accordance with an embodiment of the present invention.

For blood, different types of filters and membranes were tested in order to determine the optimal material and method for ~100% cell removal manually, without triggering cell lysis. A test was performed of the sample collection matrix using a prototype device seen in FIG. 6 that included an integrated membrane in accordance with an embodiment of the present invention. As seen in (A) of FIG. 6, an asymmetric membrane (indicated as the cell collection membrane) with a diameter of 2.5 cm and a minimum pore size of 0.2 µm was placed in a syringe filter holder (Pall Corp.). As seen in (B) of FIG. 6, the load was then passed through the asymmetric membrane using a syringe and the flow-through collected in a 2.0 ml microcentrifuge tube. The process took less than 10 seconds. The results of the tests performed with the prototype device seen in FIG. 6 are summarized in FIG. 7, which provides a graphical representation of the efficiency of the asymmetric membrane in capturing total blood cells. As shown in FIG. 6, the flow-through from the asymmetric membrane did not contain any cells thus indicating that the asymmetric membrane was able to efficiently capture 100% of the cells in sample volumes as small as 5 µl up to 150 µl of whole blood. This system can be scaled to sort ~0.5 ml of whole blood. In contrast, the flow-through from a 5 µm symmetric membrane showed a cell count of $2.7 \times 10^5$ cells/ml, demonstrating an inefficient capture of only 90% of cells (see FIG. 7(A)). Upon testing for cell lysis (hemolysis), the asymmetric membrane did not induce any hemolysis during the collection process and the collected sample was consistent with the starting control (unfiltered whole blood) (see FIG. 7(B)). In contrast, the flow-through solutions from the 5 µm and 0.8 µm membranes showed 8% and 32% hemolysis, respectively, as a result of the collection process (FIG. 7(B)). Based on these tests, the asymmetric membrane was identified as an optimized sample collection matrix.

Figure 7:
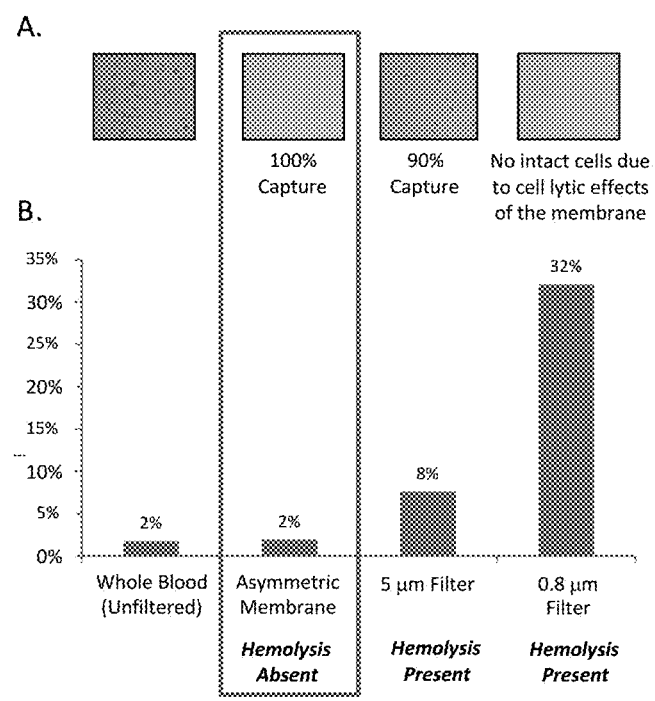
FIG. 7 illustrates a graphical representation of test results using the device of FIG. 6.

Shown in FIG. 7, the results of the tests performed with the prototype device seen in FIG. 6 demonstrate that the selected sample collection matrix was capable of ~100% of lysis free cell removal from 50 µl of whole bovine blood. Shown in (A) of FIG. 7, after filtration of 10 µl of whole bovine blood using an asymmetric microporous membrane and conventional symmetric microporous membranes, the flow-through was analyzed for the presence of cells using a light microscope. The microscopy images highlight the efficiency of the asymmetric membrane over the symmetric membranes in capturing all the cells present in 10 µl of whole blood. Shown in (B) of FIG. 7, the graph indicates that the hemolysis as measured by hemoglobin photospectroscopy in the sample processed with the asymmetric membrane is consistent with the control (unfiltered whole blood). In contrast, the flow-through solutions from the 5 µm or 0.8 µm membranes showed 8% (4×) and 32% (16×) hemolysis, respectively, thus indicating a significant increase in hemolysis due to the collection process. FIG. 7 demonstrates that the asymmetric membrane does not induce any hemolysis during cell capture—a major capability that reduces the likelihood of RNA/DNA degradation during sample collection.

Figure 8:
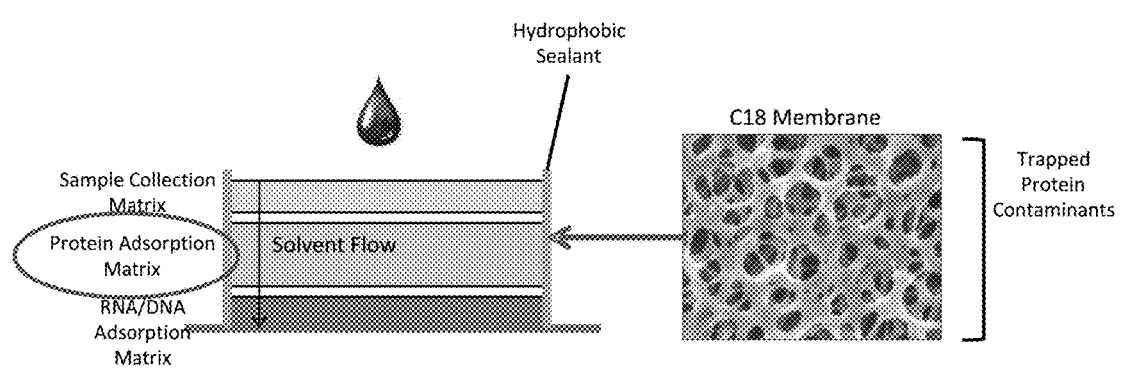
FIG. 8 illustrates the function and structure of a membrane of a protein adsorption layer or matrix in accordance with an embodiment of the present invention.

Referring to FIG. 8, a protein adsorption matrix is designed to adsorb total protein from lysed whole blood such that the RNA/DNA is preserved in a protein-free environment in the RNA/DNA adsorption matrix. As described herein, the protein adsorption matrix is capable of achieving ~100% protein depletion while recovering ~93% RNA and ~80% DNA in whole blood. Accordingly, the protein adsorption matrix is capable of preserving the integrity of the RNA/DNA from blood cell lysates. Once cells in the sample have been collected by stage one of the three-stage integrated membrane assembly (i.e., collected in the asymmetric sample collection layer or matrix; see FIG. 5), the second stage extracts and purifies RNA/DNA (in preparation for long-term preservation at ambient temperature) from the sample using the protein adsorption layer or matrix. Turning to FIG. 8, the protein adsorption matrix can be the second matrix in the integrated membrane assembly. After the blood cells are collected in the sample collection matrix, cells are lysed using the solvent (see below for details on development of the solvent), and the cell lysates subsequently enter the protein adsorption matrix.

The purpose of the protein adsorption matrix is to selectively deplete proteins from the lysates such that the nucleic acids are preserved in a protein-free environment in the RNA/DNA adsorption matrix. The protein adsorption matrix is a membrane conjugated to an 18-mer hydrocarbon chain (C18) wherein proteins are selectively adsorbed from the solution via high-affinity binding to non-polar residues. The C18 membrane enables hydrophilic molecules, such as RNA/DNA, to flow through the membrane for subsequent preservation of protein-free nucleic acids in the RNA/DNA adsorption matrix.

Figure 9:
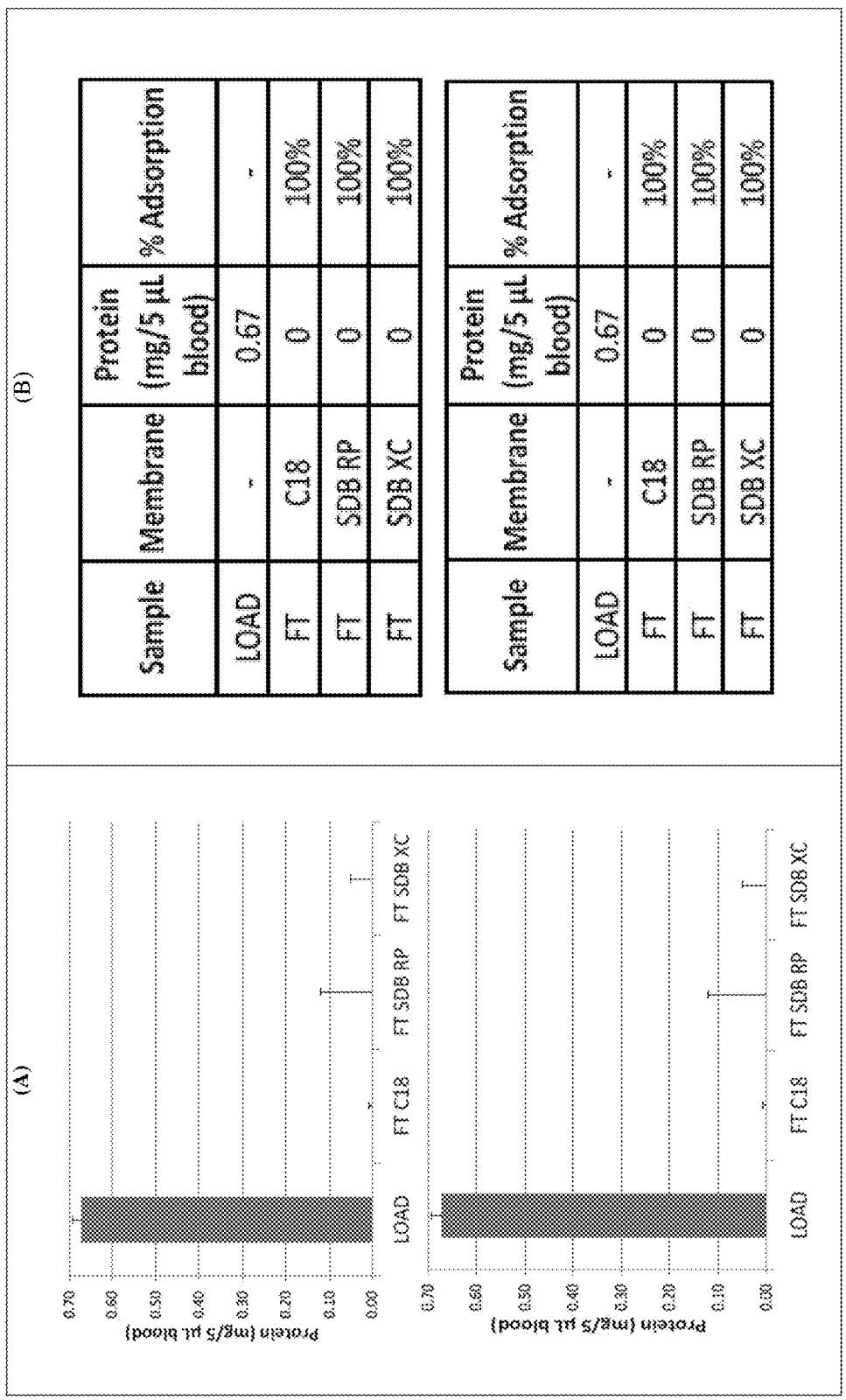
FIG. 9 illustrates total protein concentrations of lysed whole blood, both pre- and post-loading.

FIG. 9 illustrates total protein concentrations of the lysed whole blood, both pre- and post-loading. Shown in (A) of FIG. 9, a graph of the protein concentrations of the lysed whole blood, both pre- and post-loading, shows that all candidate membranes were able to achieve 100% depletion of proteins in whole bovine blood. This demonstrates a major capability of the integrated membrane assembly, as whole blood contains a nearly 3,000-fold excess of proteins over DNA. Referring to (B) of FIG. 9, a table shows the total protein concentration of the lysed whole blood prior to loading (indicated as load) and post-loading (indicated as flow-through (FT)) using the indicated membranes. The percent adsorption of total protein in the flow-through is shown to indicate membrane efficacy.

To determine total protein adsorption using the candidate reversed phase membranes, 5-50 µl of whole bovine blood was lysed in the solvent at a 1:200 dilution for a total load volume of 1 ml. The total protein concentration of the load was determined using the Pierce® 660 nm Protein Assay Reagent. FIG. 9 is a graphical representation of the data showing the protein concentration (mg/ml) of the flow-through from each of the candidate membrane. The total protein concentration of the load was 0.67 mg/ml (1/200 blood dilution), which is equivalent to 134 µg of proteins per 1 µl of blood—a value that is consistent with those observed in healthy human (103-288 µg/µl) and bovine blood. It should be noted that the SDB RP contains a sulfonic acid conjugate that enables the binding of moderately polar solutes (in this case, the guanidine HCl) present in the buffer thus leading to a large standard deviation as compared to the other membranes. Each candidate membrane showed 100% protein adsorption from 5-50 µl of lysed whole blood thus indicating that the membranes are capable of retaining 0.67 mg of protein per 4.9 cm$^2$ of membrane. These results represent a major capability of the integrated membrane assembly, as whole blood contains a 3,000-fold excess of protein over DNA. These findings firmly establish that the protein adsorption membrane will scaling of the integrated membrane to larger fluid volumes, for example, blood volumes of ~0.5 ml.

concentration is consistent with those identified in healthy bovine blood. Numerous candidate membranes were evaluated and the results are summarize in Table 1. In sum, the C18 membrane is capable of achieving 100% protein adsorption while recovering 93% of the RNA and 80% of the DNA in 5 µl of whole blood. Additional studies using larger volumes of the C-18 membrane confirmed similar results starting with 50 µl of whole bovine blood—indicating that the integrated membrane assembly technology can be scaled to process larger volumes of blood (~0.5 ml). These results demonstrate a major advantage for the integrated membrane assembly, as the system is now able to autonomously extract ~25 µg of protein-free RNA as well as ~5 µg of protein-free DNA from only 50 µl of whole blood.

Alternatives to the C18 membrane include the SDB-XC and SDB-RPS membranes. The SDB-XC membrane is a poly (StyreneDivinylBenzene (SDB)) copolymer membrane used as a reversed phase sorbent for solid phase extraction. The SDB-XC membrane is not bonded to silica but is a 100% copolymeric particle that is spherical, porous and cross-linked. It does not exhibit the secondary cationic (silanol) interactions and pH limitations common to bonded silica sorbents, so it offers more predictable and reproducible reversed phase interaction. The SDB-XC membrane may be substituted into methods that use C18 or C8 bonded silica and often demonstrates greater capacity. The structure of the SDB-XC membrane provides unique selectivity, especially in the retention of moderately polar, water-soluble analytes. However, since the SDB-XC membrane displays both aromatic and aliphatic interactions and does not display sec-

TABLE 1

| Sample | Membrane | RNA (µg/5 µL blood) | % Yield | Sample | Membrane | DNA (ng/5 µL blood) | % Yield |
|---|---|---|---|---|---|---|---|
| LOAD | — | 2.58 | 100.00 | LOAD | — | 597 | 100.00 |
| FT | C18 | 2.39 | 92.78 | FT | C18 | 481 | 80.49 |
| FT | SDB-RP | 2.19 | 84.94 | FT | SDB-RP | 231 | 38.72 |
| FT | SDB-XC | 2.12 | 82.34 | FT | SDB-XC | 214 | 35.88 |

TABLE 1 shows RNA and DNA Concentrations of the lysed whole blood, pre- and post-loading. Shown in (A) and (B) of Table 1, data for RNA (A) and DNA (B) concentration of the lysed whole blood prior to loading (indicated as load) and post-loading (indicated as flow-through (FT)) using the indicated membranes is presented. The percentage yield (% yield) of the RNA/DNA in the flow-through is shown to indicate the efficacy of the membranes. The table shows that the C18 membrane was able to recover greater than 93% of the RNA and greater than 80% in whole blood enabling the collection of ~24 µg RNA and ~5 µg of protein-free DNA per 50 µl sample.

In order to demonstrate that the reversed phase membranes are capable of selectively depleting proteins from lysed whole blood, the amount of RNA and DNA in the load was quantified and the flow-through used the Quant-It™ Assay Reagents. As shown in Table 1, the DNA concentration in the load was equivalent to 119 ng of DNA per 1 µl of blood—a value that is consistent with those observed in healthy bovine blood and only slightly higher than those observed in normal human blood (~90 ng/µl). The RNA concentration in the load was equivalent to 516 ng of RNA per 1 µl of blood. The RNA content of a typical mammalian cell is three (3) to five (5) times greater than the DNA content. As the RNA concentration (516 ng/µl) in the load is ~4× greater than the DNA concentration (119 ng), the RNA ondary cationic attraction, some existing methods may require adjustment to optimize analyte retention and elution.

The SDB-RPS (Reversed Phase Sulfonate) membrane is a poly (StyreneDivinylBenzene) copolymer membrane that has been modified with sulfonic acid groups to make it hydrophilic. SDB-RPS is not bonded to silica but is a 100% copolymeric particle that is spherical, porous and cross-linked. The sulfonation imparts unique selectivity for organic analytes that are polar in nature, such as drugs, drug metabolites, water-soluble pesticides and pesticide metabolites. SDB-RPS is also useful for comprehensive drug screening, in which a wide range of analytes are simultaneously extracted. Although SDB-RPS is sulfonated, it has much lower capacity than a typical strong cation exchanger. Because SDB-RPS displays reversed phase and cation exchange interactions, both functionalities can be considered for designing selective extractions. SDB-RPS can be used as a reversed phase sorbent and substituted into existing methods as an alternative to the C18 membrane. Organic analytes with polar character have been shown to extract better on SDB-RPS than on traditional C18 bonded silica. However, new dimensions in selectivity and elution can be achieved by considering the influence of the sulfonic acid groups to provide some cation exchange affinity for amine-containing analytes.

Development and optimization of the process for purifying RNA/DNA from whole blood prior to storage involves ensuring that buffers do not interfere with downstream processing. Guanidine hydrochloride (Gu-HCl) and 0.1% Triton X-100 selectively absorb proteins from whole cell lysates in blood and is an important component of RNA extraction buffers enabling the dissociation of nucleoprotein complexes. However, guanidine is a known contaminant that interferes with several downstream applications (e.g., gel electrophoresis, PCR). The challenge is to determine ideal concentrations of guanidine that would enable a user to rapidly and efficiently process/store RNA without needing to remove the excess guanidine prior to analysis. This was achieved by optimizing the reagents starting with commercial off-the-shelf (COTS) buffers and chemicals (see Table 2 below).

TABLE 2

| Chemical | Working Concentration | Vendor | Catalog number | Shelf-life |
|---|---|---|---|---|
| Nucleic Acid Extraction and Storage | | | | |
| Guanidine hydrochloride | 8M | Sigma-Aldrich | G7294 | 3 years |
| Sodium chloride | 50 mM | Fisher | S271-1 | 2 years |
| Triton ™ X-100 | 0.1% | Sigma-Aldrich | T8787 | 2 years |
| D-(+)-Trehalose dihydrate | 0.2M | Sigma-Aldrich | T9531 | ND |
| WFI RNase free Water | 100% | Calbiochem | 4.86505 | 2 years |
| EDTA | 10 mM | Lonza | S1201 | 2 years |
| Acetic Acid | 0.2M | Sigma-Aldrich | 330099 | 1 year |
| Nucleic Acid Elution | | | | |
| RNase free Ethanol | 95% | Sigma-Aldrich | E7148 | 2 years |
| Tris-EDTA | 50 mM | Sigma-Aldrich | T9285 | 3 years |

Table 2 lists all the custom optimized reagents and buffers used by the integrated membrane system based on the optimization of COTS components/chemicals shown above. By leveraging existing, readily available chemicals, the integrated membrane system is composed of cost-effective and established method that enhances its efficacy and acceptance within the user community.

A solvent consisting of 0.8M Gu HCl and 0.1% Triton X-100 was thus formulated and tested in order to ascertain whether the solvent is still able to recover intact RNA from blood cells (bovine blood samples) in a protein-free environment (greater than 99% protein depletion). To visualize the RNA on an analytical gel and thus measure the integrity of the RNA, the level of the isolated RNA was increased by isolating only leukocytes from whole blood using the 1× Red Blood Cell Lysis Buffer (BioLegend, San Diego, Calif.). By enriching for leukocytes, the integrated membrane system is challenged by introducing a sample that is likely to have a higher RNase/DNase content due to the presence of intracellular nucleases, as compared to whole blood. $2\times10^6$ blood cells were lysed with solvent containing 0.8M Guanidine HCl and 0.1% Triton X-100. Upon lysis, the blood cell lysates were applied to a pre-activated C18 membrane. Analysis of the flow-through for (1) RNA/DNA integrity occurred using analytical gels, and (2) total protein content using the Pierce® 660 nm Protein Assay. As shown in (C) of FIG. 10, the RINs for both the lysate and the flow-through are 1.6 and 1.5, respectively, indicating that the processing step was able to preserve the integrity of the total RNA. Densitometry analysis was then performed to compare the relative amounts of 28s rRNA present in the lysate (indicated as Pre-C18) and flow-through (indicated as Post-C18). The amount of recovered RNA is greater than 82% of the RNA present in the lysate, indicating that the solvent is capable of efficiently extracting RNA from blood cells. As shown in (B) of FIG. 10, the blood cell lysates contained 61 µg of total protein prior to loading onto a C18 membrane, which is consistent with the amount of protein present in $2\times10^6$ cells, as a human lymphocyte contains 0.1±0.04 ng protein. Upon loading, the flow-through from the C18 membrane (indicated as Post-C18) showed greater than 99.74% depletion of the proteins present in the lysate. The results here are consistent with previous data showing that the C18 membrane has a binding capacity of up to 0.67 mg of protein per 25 mm disk.

Figure 10:
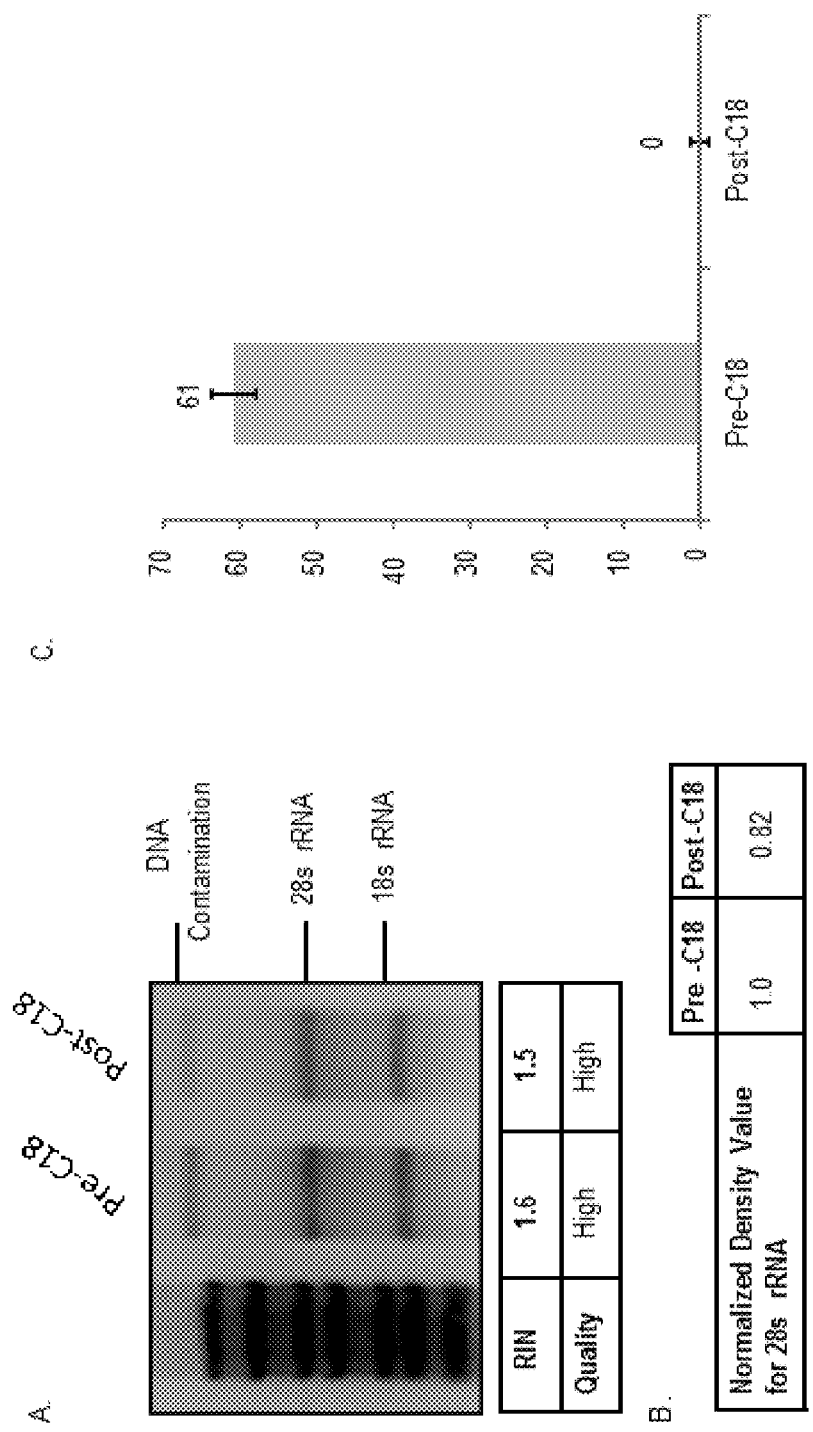
FIG. 10 illustrates an analysis of the total RNA present in blood cell lysates, pre- and post-loading, using 0.8M Guanidine HCl.

FIG. 10 illustrates—an analysis of the total RNA present in blood cell lysates, pre- and post-loading, using 0.8M Guanidine HCl. As seen in (A) of FIG. 10, the 0.8% formaldehyde-treated agarose gel shows the extracted total RNA from blood cell lysates prior to loading (indicated as Pre-C18) and post-loading (indicated as Post-C18). The ratio of the optical density (OD) of the 28 s rRNA to the OD of the 16 s rRNA was determined to obtain the RNA integrity number (RIN) for the total RNA obtained from blood cell lysates pre- and post-loading. The RIN values for both the lysate and the flow-through are both greater than 1 indicating the presence of high-quality RNA. Turning to (B) of FIG. 10, the amount of recovered RNA is ~82% of the RNA present in the lysate, indicating that the solvent is capable of efficiently extracting RNA from blood cells. Shown in (C) of FIG. 10, the graph illustrates the total protein concentration of the blood cell lysate pre- and post-C18 loading. The error bars represent standard deviations determined from a single sample run analyzed in triplicate. The graph confirms that the C18 membrane was able to achieve greater than 99.74% depletion of proteins from blood cell lysates. The results confirm that the solvent consisting of 0.8M Gu-HCl and 0.1% Triton X-100 was able to recover high-quality total RNA with ~100% protein depletion from blood cell lysates. This is a major capability of the integrated membrane system as the user will now be able to rapidly process/store the RNA without needing to remove the excess guanidine prior to analysis—a laborious step that increases operator error/variation.

Figure 11:
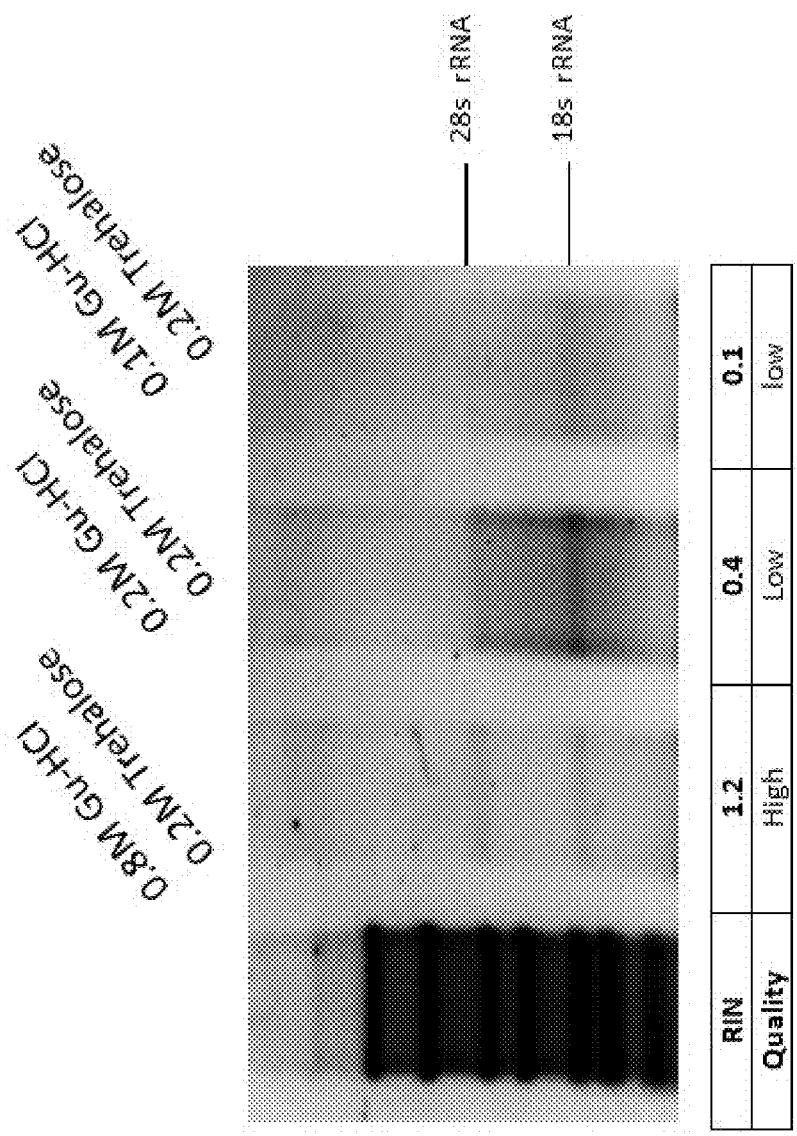
FIG. 11 illustrate an analysis of the RNA samples upon 24-hour storage with various concentrations of Guanidine HCl.

FIG. 11 illustrate an analysis of the RNA samples upon 24-hour storage with various concentrations of Guanidine HCl. The 0.8% formaldehyde-treated agarose gel shows the RNA samples after incubation for 24 hours in the presence of varying concentrations of Gu-HCl and 0.2M trehalose. Densitometric analysis was performed to obtain the RNA Integrity Number (RIN). As shown in the panel, the RIN for the RNA sample stored in 0.8M Gu-HCl was greater than 1, indicating the presence of non-degraded, high-quality RNA. In contrast, the RIN values for the RNA sample stored in 0.2 and 0.1M Gu-HCl were both less than 1, indicating the presence of degraded, poor-quality RNA. The figure demonstrates that 0.2 Gu HCl is the optimal IMPRINT concentration.

While purified DNA may be stored for weeks at ambient temperatures, purified RNA may only be stored for hours at room temperature. The challenge therefore was to identify the proper storage conditions to store highly labile molecules, such as RNA, for periods longer than a few hours at room temperature. The integrated membrane system employs a method by which purified RNA/DNA is stored in a dry state—a mechanism that inhibits RNA/DNA biodegradation by hydrolysis thus enabling the storage of RNA/DNA for longer periods at ambient temperatures.

Figure 12:
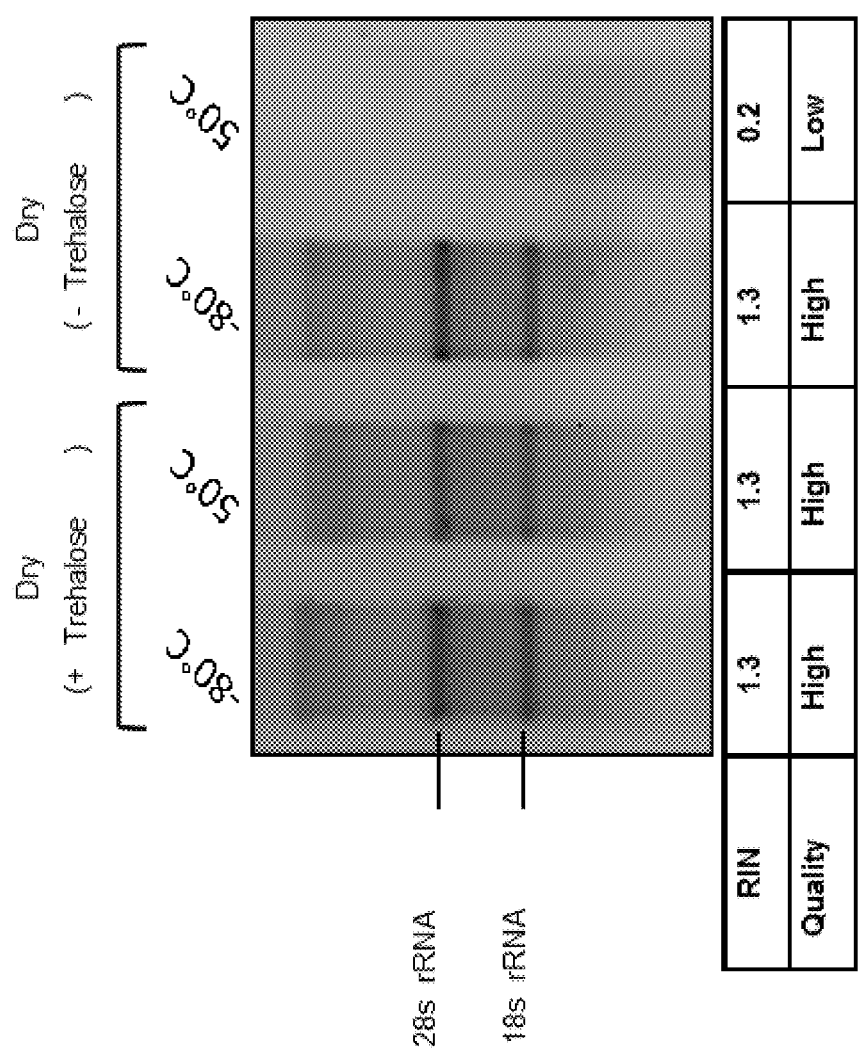
FIG. 12 illustrates an analysis of the purified RNA samples upon dry storage for 8 days at various temperatures.

FIG. 12 illustrates an analysis of the purified RNA samples upon dry storage for 8 days at various temperatures. The 0.8% formaldehyde-treated agarose gel shows the RNA samples after incubation for 8 days at −80° C. (as a positive control) or 50° C. Densitometric analysis was performed on the analytical gel using the ImageJ software to obtain the RNA Integrity Number (RIN) (shown in the panel below). The RINs for the purified RNA stored in the presence of trehalose were comparable (RIN=1.3) among samples incubated at either −80° C. or 50° C. for 8 days. In contrast, the RIN for the purified RNA stored in the absence of trehalose decreased significantly with a value of 0.2, as compared to the RIN of the −80° C. control (RIN=1.3). FIG. 12 shows the stability of the dehydrated RNA in the presence of trehalose when stored for at least 8 days at 50° C. (equivalent to 56 days at 22° C.).

As previously described, the isolated RNA/DNA as extracted from whole blood using the integrated membrane is free from protein contaminants. Tables 1-2 show representative data set wherein the integrated membrane was able to recover ~93% RNA and ~80% of the DNA while achieving 100% protein depletion. Given that relatively large amounts of purified RNA/DNA would be required to assess the stability of the RNA/DNA using standard agarose gel electrophoresis, ~400 µg of RNA and ~100 µg DNA was prepared from $2 \times 10^7$ leukocytes (as isolated from heparinized bovine blood) using a standard phenol:chloroform extraction method—a method that enables the large-scale preparation of protein-free RNA/DNA. This allowed for preparation of RNA/DNA stocks mimicking those prepared using the integrated membrane. The RNA was prepared using a standard phenol: chloroform extraction, as described previously. The dried RNA was prepared by pipetting 2 µg of purified RNA onto a matrix in the presence and absence of trehalose (a chemical stabilizer). Upon drying, the RNA was stored at −80° C. (as a positive control) or 50° C. for 8 days. It should be noted that storage for 8 days at 50° C. is equivalent to 56 days at 22° C. according to the accelerated aging theory. To assess the integrity of the RNA, samples were solubilized in nuclease-free water, electrophoresed in a 0.8% formaldehyde-treated agarose gel and visualized using SYBR Green II (Sigma, St. Louis, Mo.). As shown in FIG. 12, when the purified RNA was stored in a dry state at 50° C., the RNA remained stable only in the presence of trehalose as indicated by the presence of distinct 28s and 18s rRNA bands. In contrast, when the purified RNA was stored in the absence of trehalose, the sample stored at 50° C. showed complete degradation, as evidenced by the disappearance of both the 28s and 18s rRNA bands. Densitometry analysis with ImageJ software was performed to compute RNA integrity number (RIN). As the RIN is dependent on the tissue from which the RNA was extracted, the RIN of the sample stored at −80° C. was used as a standard for each sample type (Life Technologies, 2012). Typically, RIN values that are greater than 1 are indicative of intact RNA (Life Technologies, 2012). As indicated in FIGS. 1-11, the RINs for the purified RNA stored in the presence of trehalose were comparable (RIN=1.3) among samples incubated at either −80° C. or 50° C. for 8 days. In contrast, the RIN for the purified RNA stored in the absence of trehalose decreased significantly with a value of 0.2, as compared to the RIN of the −80° C. control (RIN=1.3). These results thus far show that the dehydrated RNA is required to be stored in the presence of trehalose in order to achieve long-term RNA preservation (i.e., 56 days at 22° C.).

Figure 13:
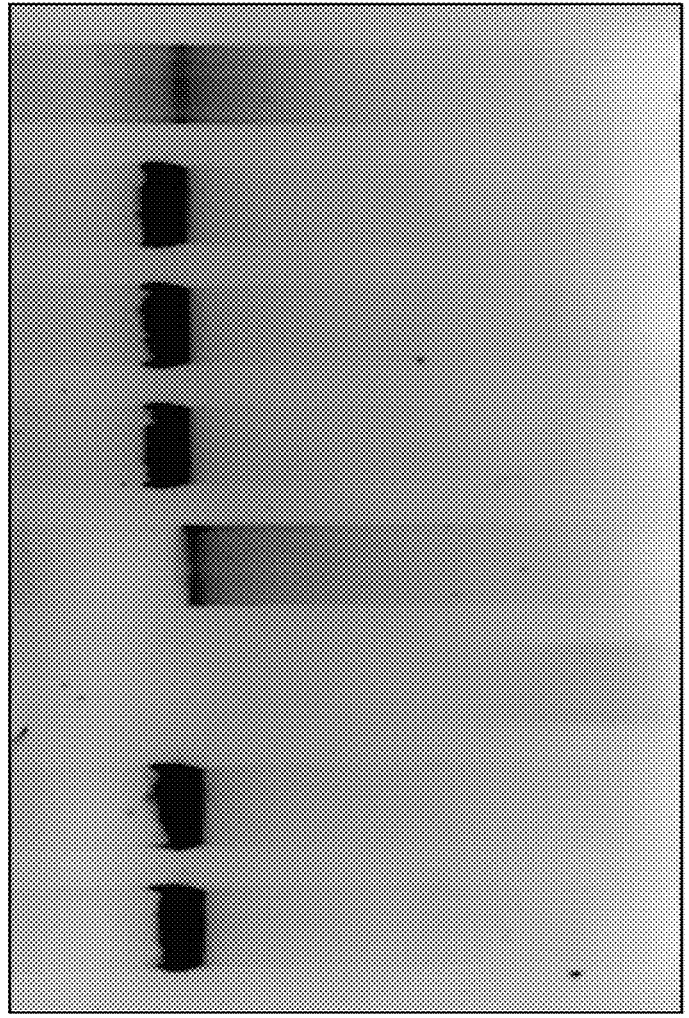
FIG. 13 illustrates the stability of the purified DNA in a dry state when stored for up to 24 hours at 50° C. temperatures.

The ability of the integrated membrane system to enable the long-term storage of the purified DNA at ambient temperatures was determined. The stability of dried DNA (as compared to DNA stored in nuclease-free water) was tested after incubation for 24 hours at 37° C. and 50° C., which are temperatures that mimic 3 and 7 days respectively of storage at 22° C. The dried DNA was prepared by pipetting 0.5 µg of purified DNA onto a matrix in the presence of trehalose (a chemical stabilizer). Upon drying, the DNA was stored at −20° C. (as a positive control), 37° C. and 50° C. for 24 hours. DNA samples stored in nuclease-free water were prepared by pipetting 0.5 µg of purified DNA in 10 µl of nuclease-free water and storing the samples at −20° C. (as a positive control), 37° C. and 50° C. for 24 hours. To assess the integrity of the DNA, samples were solubilized (if dried) in nuclease-free water, electrophoresed in a 0.8% agarose gel and visualized using ethidium bromide. As shown in FIG. 13 the integrated membrane system is capable of preserving DNA for 24 hours at 50° C., which is equivalent to 7 days of storage at 22° C. Moreover, it was also demonstrated that DNA stored in nuclease-free water or dry in the presence of protein contaminants is not stable thus exhibiting the need for purifying the DNA prior to storage (FIG. 13, lanes marked by +protein contaminants). The ability of the integrated membrane system to purify DNA/RNA prior to dry storage is thus a major advantage of the system enabling for longer periods of DNA/RNA storage at ambient temperatures. These results demonstrate the capability of the integrated membrane technology at preserving DNA/RNA at ambient conditions for greater than 20 years.

Turning to FIG. 13, the 0.8% agarose gel shows the DNA samples after incubation for 24 hours at −20° C., 37° C. and 50° C. in the presence and absence of cell lysates. FIG. 13 shows the stability of the purified DNA in a dry state when stored for up to 24 hours at 50° C. temperatures (equivalent to 7 days at 22° C.). In contrast, DNA stored in the presence of water is shown to fully degrade at 50° C. after less than 24 hours of storage. Moreover, DNA stored in nuclease-free water or dry in the presence of protein contaminants is shown to degrade significantly thus showing the need for purifying the DNA prior to storage.

Successful recovery of ~93% RNA and ~80% DNA was obtained while achieving greater than 99% protein depletion from whole blood processed through the integrated membranes. Furthermore, the extracted DNA and RNA were shown to be well preserved for greater than 50 days (accelerated aging tests).

The integrated membrane assemblies of the present invention are shown to have numerous technical advantages including, but not limited to, the examples provided herein. For example, the integrated membrane assemblies allow proteins to be captured in their native states with the protein adsorption layer via use of a non-denaturing solvent that acts to simply/passively extract intracellular proteins. In another example, RNA/DNA is extracted, purified and preserved without the use of protein denaturants which enables a user to directly use the RNA/DNA upon elution from the matrix (use of protein denaturants (as are typically used in sample processing) requires the user to perform additional steps prior to analysis, as protein denaturants can interfere with many downstream applications). In an additional example, the integrated membrane facilitates one-step extraction, purification and long-term preservation of protein/DNA/RNA molecules at near room temperature for point-of-service (POS) use (the user is simply required to apply the sample on the membrane followed by the solvent and wait until the membrane is ready to be peeled and dried). In yet another example, the integrated membrane is compatible with Clinical Laboratory Improvement Amendmentswaived (CLIA-waived) devices (e.g., the integrated membrane employs a hands-free methodology for protein/RNA/DNA collection that is so simple and accurate that it renders the likelihood of erroneous results negligible). In a further example, the integrated membrane works with a minimal sample volume (i.e., the integrated membrane captures adequate amounts of protein/RNA/DNA for subsequent analysis from blood volumes as low as 10 μl). In yet another example, the integrated membrane captures substantially all proteins and nucleic acids from minimal volumes (5-10 μl) of whole blood. In another example, the integrated membrane is able to process each blood sample in less than two minutes, and preferably within 1.5 minutes (i.e., the fluid sample passes through the integrated membrane and the layers are ready for subsequent use by a user within 1.5 minutes). In an additional example, the protein/nucleic acid adsorption layers are impregnated with anhydrobiotic agents that stabilize RNA/DNA molecules for long-term storage at ambient conditions, as described herein.

The integrated membrane assemblies of the present invention have numerous economic advantages including, but not limited to, the following examples. For example, the integrated membrane can be assembled from inexpensive commercial off-the-shelf (COTS) materials at an estimated cost of $2 per sample. In another example, the integrated membrane is stored at near-room temperature before and after sample application, which eliminates the need for laboratory freezers (allowing for ambient storage conditions with minimal logistic burden). In an additional example, minimal volume is needed to store the layers as each sample collection blot is approximately 25 mm in diameter (providing compact package volume).

Although the present invention has been discussed above in connection with blood, the present invention is not limited to that particular fluid and may also be used with any fluid that may contain nucleic material including, without limitation, bodily fluids (e.g., urine, semen, saliva, lymphatic fluid, etc.) or non-bodily fluids (e.g., water). A user may also choose not to use the lyse buffer/solvent if the user wishes to preserve cells such that foreign proteins and/or nucleic freely circulating in a subject's bloodstream or other bodily fluid (e.g., the proteins and/or nucleic material of bacteria or other organisms in a subject's bloodstream) may be collected.

Furthermore, the integrated membrane can be used to perform moeity specific sample extraction from a variety of complex sample matrix (e.g., blood, food, soil, etc.) in a flow through process. Even dry material can be used because the material can be buffer, as described above. The above described embodiments demonstrates separation of classes of biological material, such as cells, proteins and nucleic acids (DNA/RNA) fully preserved from whole blood. The subtlety here is that for many components, this has to be done rapidly—otherwise components such as proteins and RNA may degrade. As shown above, material from within cells can be extracted (by using lysing buffers). Other manifestations include targeted extraction, e.g., a specific protein or miRNA. In that example, a membrane with conjugate components can be integrated in the membrane assembly to extract just that targeted component. All this done in a single flow-through process after the best sequence of sorting has been determined. As described above, if a user desires to obtain nucleic acids, then the user determines that the user need to filter out the cells and then the proteins, or otherwise the nucleic acids can degrade.

Likewise, although the integrated membrane disclosed above has been discussed above in connection with a canister, the present invention is not limited to that specific construction and, in particular, the integrated membrane may be incorporated into various other constructs including, without limitation, a bandage, a swab, filter, or any other object used for, or capable of being used for, collecting a fluid in which proteins and/or nucleic material may be found.

In an alternative, an integrated membrane may be placed directly in a syringe or syringe attachment. The fluid sample (e.g., blood) is then pumped across the integrated membrane (either during uptake or dispense mode). In an example of an integrated membrane in a syringe attachment, the syringe attachment may be matingly engaged to a hypodermic needle on one end and a syringe on the other end, with the integrated membrane disposed within the syringe attachment. After blood is drawn, the syringe and needle are disengaged from the attachment and the apertures (where the attachment had engaged syringe and needle) sealed. As blood is drawn, the blood is dispensed across the layers of the integrated membrane, with the layers automatically processing the blood in the manner described above. The fluid remaining after passing through the integrated membrane exits the attachment and enters the syringe. The fluid within the syringe may be stored in a vial or other container for subsequent use or discarded with the syringe.

In addition, the claimed invention is not limited in size and may be constructed in various sizes in which the same or similar principles of operation as described above would apply. Furthermore, the figures (and various components shown therein) of the specification are not to be construed as drawn to scale.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention.

What is claimed is:

1. An apparatus for separating and preserving biomolecules of a biological fluid, the apparatus comprising:
    an assembly comprising:
        sides forming a hollow shape with an opening at each of two ends forming a first opening and a second opening; and
        two matrix layers positioned within the hollow shape between the two ends, the two matrix layers comprising a first matrix layer and a second matrix layer, the two matrix layers each spanning the hollow shape and contacting the sides of the assembly, the sides of the assembly being reversibly and hydrophobically sealed with the two matrix layers to actuate a flow of the biological fluid, the flow having a direction from the first matrix layer to the second matrix layer,
            the first matrix layer configured to receive the biological fluid and a lysis buffer, the first matrix layer comprising a first membrane layer configured to trap proteins and to allow nucleic acids to flow through onto the second matrix layer, and
            the second matrix layer comprising a second membrane layer configured to selectively bind nucleic acids, the second matrix layer configured to separate from the assembly in a direction away from the first matrix layer.

2. The apparatus of claim 1, wherein the first membrane layer is a hydrophobic protein adsorption membrane.

3. The apparatus of claim 2, wherein the hydrophobic protein adsorption membrane is selected from the group consisting of cellulose or silica membranes conjugated with C8 or C18 polymeric chains and styrene divinyl benzene (SDB) copolymer membranes.

4. The apparatus of claim 1, wherein the second membrane layer is a positively charged membrane.

5. The apparatus of claim 1, wherein the second membrane layer is a positively charged cellulose or silica membrane.

6. The apparatus of claim 1, wherein the second membrane layer comprises at least one line of weakness forming at least two sections of the second membrane layer, allowing for independent removal of at least one section of the second membrane layer from the rest of the second membrane layer.

7. The apparatus of claim 1, wherein the second membrane layer comprises a plurality of lines of weakness forming a plurality of independently removable sections of the second membrane layer.

8. The apparatus of claim 1, further comprising a cover portion overlaying the first opening of the assembly, the cover portion having a neck with an aperture disposed on a distal end of the neck away from the first opening of the assembly, the aperture in fluid connection with the first opening of the assembly for receiving the biological fluid.

9. The apparatus of claim 1, wherein the first matrix layer is configured to separate a biological fluid comprising cells.

10. The apparatus of claim 1, wherein the first matrix layer is configured to separate a biological fluid selected from whole blood, partially fractionated blood, and/or blood plasma.

11. An apparatus for separating and preserving biomolecules of a biological fluid, the apparatus comprising:
    an assembly comprising:
        sides forming a hollow shape with an opening at each of two ends forming a first opening and a second opening; and
        three matrix layers positioned within the hollow shape between the two ends, the three matrix layers comprising a first matrix layer, a second matrix layer, and a third matrix layer, the three matrix layers each spanning the hollow shape and contacting the sides of the assembly, the sides of the assembly being reversibly and hydrophobically sealed with the three matrix layers to actuate a flow of the biological fluid, the flow having a direction from the first matrix layer to the second matrix layer to the third matrix layer,
            the first matrix layer configured to receive the biological fluid and a lysis buffer, the first matrix layer comprising a first membrane layer configured to trap membranes and to allow proteins and nucleic acids to flow through onto the second matrix layer,
            the second matrix layer comprising a second membrane layer configured to trap proteins and to allow nucleic acids to flow through onto the third matrix layer, and
            the third matrix layer comprising a third membrane layer configured to selectively bind nucleic acids, the second and/or third matrix layers configured to independently separate from the assembly in a direction away from the first matrix layer.

12. The apparatus of claim 11, wherein the first membrane layer is an asymmetric membrane.

13. The apparatus of claim 11, wherein the second membrane layer is a hydrophobic protein adsorption membrane.

14. The apparatus of claim 13, wherein the hydrophobic protein adsorption membrane is selected from the group consisting of cellulose or silica membranes conjugated with C8 or C18 polymeric chains and styrene divinyl benzene (SDB) copolymer membranes.

15. The apparatus of claim 11, wherein the third membrane layer is a positively charged membrane.

16. The apparatus of claim 11, wherein the third membrane layer is a positively charged cellulose or silica membrane.

17. The apparatus of claim 11, wherein the second and/or third membrane layers comprise at least one line of weakness forming at least two sections of the second and/or third membrane layers, allowing for independent removal of at least one section of the second and/or third membrane layer from the rest of the second and/or third membrane layers.

18. The apparatus of claim 11, wherein the second and/or third membrane layers comprise a plurality of lines of weakness forming a plurality of independently removable sections.

19. The apparatus of claim 11, further comprising a cover portion overlaying the first opening of the assembly, the cover portion having a neck with an aperture disposed on a distal end of the neck away from the first opening of the assembly, the aperture in fluid connection with the first opening of the assembly for receiving the biological fluid.

20. The apparatus of claim 11, wherein the first matrix layer is configured to separate a biological fluid comprising cells.

21. The apparatus of claim 11, wherein the first matrix layer is configured to separate a biological fluid selected from whole blood, partially fractionated blood, and/or blood plasma.

* * * * *